(12) United States Patent
Fägerhag et al.

(10) Patent No.: US 6,630,509 B2
(45) Date of Patent: Oct. 7, 2003

(54) PHENALKYLOXY-PHENYL DERIVATIVES

(75) Inventors: Jonas Fägerhag, Mölndal (SE); Lanna Li, Mölndal (SE); Eva-Lotte Lindstedt Alstermark, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/148,824

(22) PCT Filed: Nov. 29, 2000

(86) PCT No.: PCT/SE00/02383

§ 371 (c)(1),
(2), (4) Date: Jun. 3, 2002

(87) PCT Pub. No.: WO01/40170

PCT Pub. Date: Jun. 7, 2001

(65) Prior Publication Data

US 2003/0018207 A1 Jan. 23, 2003

(30) Foreign Application Priority Data

Dec. 3, 1999 (SE) ................................. 9904418
Dec. 3, 1999 (SE) ................................. 9904422

(51) Int. Cl.[7] ............................................. A61K 31/27
(52) U.S. Cl. .................. 514/476; 558/51; 558/423; 564/192; 568/33; 568/77; 514/513; 514/517
(58) Field of Search .................. 514/513, 517, 514/476; 568/33, 77; 558/51, 423; 564/192

(56) References Cited

FOREIGN PATENT DOCUMENTS

| EP | 0641766 | 3/1995 |
|---|---|---|
| WO | 9911255 | 3/1999 |
| WO | 9962870 | 12/1999 |
| WO | 9962871 | 12/1999 |
| WO | 9962872 | 12/1999 |

*Primary Examiner*—Joseph K. McKane
*Assistant Examiner*—Robert Shiao
(74) *Attorney, Agent, or Firm*—White & Case LLP

(57) ABSTRACT

The present invention relates to certain phenalkyloxy-phenyl derivatives of formula (I)

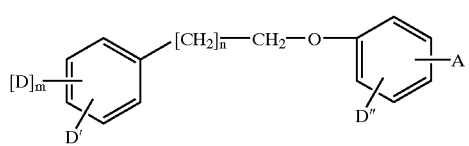

and analogs, to a process for preparing such compounds, which compounds have utility in treating clinical conditions associated with insulin resistance, to methods for their therapeutic use and to pharmaceutical compositions containing them.

12 Claims, No Drawings

PHENALKYLOXY-PHENYL DERIVATIVES

This application is a 371 of PCT/SE00/02383 filed Nov. 29, 2000.

FIELD OF INVENTION

The present invention relates to certain phenalkyloxy-phenyl derivatives of formula I and analogs, to a process for preparing such compounds, having the utility in clinical conditions associated with insulin resistance, to methods for their therapeutic use and to pharmaceutical compositions containing them.

BACKGROUND OF THE INVENTION

Insulin resistance, defined as reduced sensitivity to the actions of insulin in the whole body or individual tissues such as skeletal muscle, myocardium, fat and liver prevail in many individuals with or without diabetes mellitus. The insulin resistance syndrome, IRS, refers to a cluster of manifestations including insulin resistance with accompanying hyperinsulinemia, possibly type 2 diabetes mellitus, arterial hypertension, central (visceral) obesity, dyslipidemia observed as deranged lipoprotein levels typically characterised by elevated VLDL (very low density lipoproteins) and reduced HDL (high density lipoproteins) concentrations, the presence of small, dense LDL (Low Density Lipoprotein) particles and reduced fibrinolysis.

Recent epidemiological research has documented that individuals with insulin resistance run a greatly increased risk of cardiovascular morbidity and mortality, notably suffering from myocardial infarction and stroke. In non-insulin dependent diabetes mellitus these atherosclerosis related conditions cause up to 80% of all deaths.

In clinical medicine there is at present only limited awareness of the need to increase the insulin sensitivity in IRS and thus to correct the dyslipidemia which is considered to cause the accelerated progress of atherosclerosis.

Furthermore there is at present no pharmacotherapy available to adequately correct the metabolic disorders associated with IRS. To date, the treatment of type 2 diabetes mellitus has been focused on correction of the deranged control of carbohydrate metabolism associated with the disease. Stimulation of endogenous insulin secretion by means of secretagogues, like sulphonylureas, and if necessary administration of exogenous insulin are methods frequently used to normalise blood sugar but that will, if anything, further enhance insulin resistance and will not correct the other manifestations of IRS nor reduce cardiovascular morbidity and mortality. In addition such treatment involves a significant risk of hypoglycemia with associated complications.

Other therapeutic strategies have focused on aberrations in glucose metabolism or absorption, including biguanides, such as methformin, or glucosidase inhibitors, such as acarbose. Although these agents have been efficacious to a degree, their limited clinical effect is associated with side effects.

A novel therapeutic strategy involves the use of insulin sensitising agents, such as the thiazolidinediones which at least in part mediate their effects via an agonistic action on nuclear receptors. Ciglitazone is the prototype in this class. In animal models of IRS these compounds seem to correct insulin resistance and the associated hypertriglyceridaemia and hyperinsulinemia, as well as hyperglycaemia in diabetes, by improving insulin sensitivity via an effect on lipid transport and handling primarily in adipocytes, leading to enhanced insulin action in skeletal muscle, liver and adipose tissue.

Ciglitazone as well as later described thiazolidinediones in clinical development either have been discontinued reportedly due to unacceptable toxicity or show inadequate potency. Therefore there is a need for new and better compounds with insulin sensitising properties.

Other therapeutic strategies have focused on aberrations in glucose metabolism or absorption, including biguanides, such as methformin, or glucosidase inhibitors, such as acarbose. Although these agents have been efficacious to a degree, their limited clinical effect is associated with side effects.

A novel therapeutic strategy involves the use of insulin sensitising agents, such as the thiazolidinediones which at least in part mediate their effects via an agonistic action on nuclear receptors. Ciglitazone is the prototype in this class. In animal models of IRS these compounds seem to correct insulin resistance and the associated hypertriglyceridemia and hyperinsulinemia, as well as hyperglycemia in diabetes, by improving insulin sensitivity via an effect on lipid transport and handling, leading to enhanced insulin action in skeletal muscle, liver and adipose tissue.

Ciglitazone as well as later described thiazolidinediones in clinical development either have been discontinued reportedly due to unacceptable toxicity or show inadequate potency.

Therefore there is a need for new and better compounds with insulin sensitising properties.

DESCRIPTION OF THE INVENTION

The invention relates to compounds of the general formula (I)

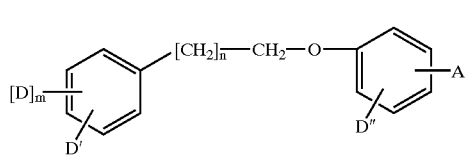

and stereo and optical isomers and racemates thereof as well as pharmaceutically acceptable salts, prodrugs, solvates and crystalline forms thereof, in which formula A is situated in the ortho, meta or para position and represents

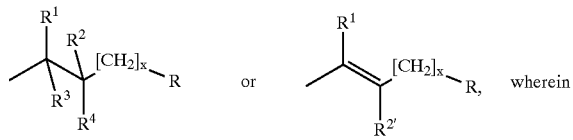

R is cyano, when X is O, and when X is 1 then R is;
— $BR^a$ or $SCOR^a$, wherein B is O, S, SO or SO, (preferably B is O or S), wherein $R^a$ represents hydrogen, alkyl, aryl or alkylaryl (preferably $R^a$ is selected from hydrogen, alkyl and alkyaryl) and wherein the alkyl, aryl or alkylaryl group is optionally substituted one or more times by $R^b$, wherein $R^b$ represents alkyl, aryl, alkylaryl, cyano, —$NR^cR^c$, =O, halogen, —OH, —SH, —Oalkyl, —Oaryl, —Oalkylaryl, —$COR^c$, —$SR^d$, —$SOR^d$, or —$SO_2R^d$ (preferably $R^b$ is selected from alkyl, aryl, alkylaryl, cyano, —$NH_2$, =O, halogen and —OH), wherein $R^c$ represents hydrogen, alkyl, aryl or alkylaryl and $R^d$ represents alkyl, aryl or alkylaryl;
—$BB^1R^a$, wherein $B^1$ is O when B is S, SO or $SO_2$ or $B^1$ is S, SO or $SO_2$ when B is O, and wherein B and $R^a$ are as defined above;

or alternatively R is —NR$^a$R$^a$, wherein each R$^a$ is the same or different and wherein R$^a$ is defined above;

R$^2$ represents alkyl, halogen (preferably bromo, chloro or iodo), aryl, alkylaryl, alkenyl, alkynyl, nitro or cyano and wherein the alky, aryl, alkenyl, alkylaryl and alkynyl group is optionally substituted by R$^b$, wherein R$^b$ is as defined above;

—BR$^a$ wherein B and R$^a$ are as defined above;
—SO$_2$NR$^a$R$^f$, wherein R$^f$ represents hydrogen, alkyl, acyl, aryl or alkylaryl and R$^a$ is as defined above;
—SO$_2$OR$^a$, wherein R$^a$ is as defined above;
—OCONR$^f$R$^a$, wherein R$^f$ and R$^a$ are as defined above;
—NR$^c$COOR$^d$, wherein R$^c$ and R$^d$ are as defined above;
—NR$^c$COR$^a$, wherein R$^c$ and R$^d$ are as defined above;
—CONR$^c$R$^a$, wherein R$^c$ and R$^a$ are as defined above;
—NR$^c$SO$_2$R$^d$, wherein R$^a$ and R$^d$ are as defined above;
—NR$^c$CONR$^a$R$^k$, wherein R$^a$ and R$^c$ are as defined above and R$^k$ represents hydrogen, alkyl, aryl, or alkylaryl;

alternatively R$^2$ is —NR$^c$R$^a$, wherein R$^c$ and R$^d$ are as defined above;

R$^1$, R$^3$ and R$^4$ are the same or different and each represents hydrogen, alkyl, aryl, alkenyl, alkynyl, cyano, halogen or alkylaryl (preferably R$^1$, R$^3$ and R$^4$ are independently selected from hydrogen or alkyl, ideally R$^1$, R$^3$ and R$^4$ are hydrogen) wherein the alkyl, aryl, alkenyl or alkynyl group is optionally substituted by R$^b$;

n is an integer from 1 to 6 (preferably n is an integer from 1 to 3, ideally n is 1);

X is an integer 0 or 1 (preferably X is 1);

m is an integer 0 or 1 (preferably m is 1);

D is situated in the ortho, meta or para position (preferably D is situated in the para position) and represents alkyl, acyl, aryl, alkylaryl, halogen, —CN and NO$_2$, wherein the alkyl, aryl, or alkylaryl group is optionally substituted by R$^b$;

—NR$^c$COOR$^a$, wherein R$^c$ and R$^a$ are as defined above;
—NR$^c$COR$^a$, wherein R$^c$ and R$^a$ are as defined above;
—NR$^c$R$^a$, wherein R$^c$ and R$^a$ are as defined above;
—NR$^c$SO$_2$R$^d$, wherein R$^c$ and R$^d$ are as defined above;
—NR$^c$CONR$^k$R$^c$, wherein R$^a$, R$^c$ and R$^k$ are as defined above;
—NR$^c$CSNR$^a$R$^k$, wherein R$^a$, R$^c$ and R$^k$ are as defined above;
—OR$^a$, wherein R$^a$ is as defined above;
—OSO$_2$R$^d$, wherein R$^d$ is as defined above;
—SO$_2$R$^d$, wherein R$^d$ is as defined above;
—SOR$^d$, wherein R$^d$ is as defined above;
—SR$^c$, wherein R$^c$ is as defined above;
—SO$_2$NR$^a$R$^f$, wherein R$^f$ and R$^a$ are as defined above;
—SO$_2$OR$^a$, wherein R$^a$ is as defined above;
—CONR$^c$R$^a$, wherein R$^c$ and R$^a$ are as defined above;
—OCONR$^f$R$^a$, wherein R$^f$ and R$^a$ are as defined above;

D' is situated in the ortho, meta or para position (preferably D' is situated in the ortho or meta position) and represents hydrogen, alkyl, acyl, aryl, alkylaryl, halogen, —CN, —NO$_2$,
—NR$^f$R$^b$, wherein R$^f$ and R$^b$ are as defined above;
—OR$^f$, wherein R$^f$ is as defined above;
—OSO$_2$R$^d$, wherein R$^d$ is as defined above;

D" is situated in the ortho, meta or para position (preferably D" is situated in the ortho or meta position) and represents hydrogen, alkyl, acyl, aryl, alkylaryl, halogen, —CN, —NO$_2$,
—NR$^f$R$^b$ wherein R$^f$ and R$^b$ are as defined above;
—OR$^f$, wherein R$^f$ is as defined above;
—OSO$_2$R$^d$, wherein R$^d$ is as defined above.

For ease of reference the definitions of formula I above is henceforth referred to as defined in Category A. Unless otherwise stated the definitions of the various substituents are as defined under Category A throughout the present application.

The compounds of the formula I are surprisingly effective in conditions associated with insulin resistance.

Category A2: preferred compounds of the present invention are those of formula I as defined above in category A, but wherein A is situated in the meta or para position (preferably A is situated in the para position) and represents

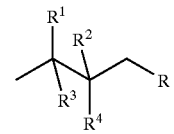

wherein R is
—BR$^a$ wherein R$^a$ is as defined above;
—SCOR$^a$ wherein R$^a$ is as defined above;
—OSO$_2$R$^a$, wherein R$^a$ is as defined above;

R$^1$, R$^3$ and R$^4$ are the same or different and each represents hydrogen, alkyl, aryl, alkenyl, alkynyl or cyano, wherein the alkyl, aryl, alkenyl or alkynyl group is optionally substituted by R$^b$;

R$^2$ represents represents alkyl, aryl, alkenyl, cyano or alkynyl and wherein the alkyl, aryl, alkenyl and alkynyl group is optionally substituted by R$^b$; —BR$^a$;
—OSO$_2$R$^a$, wherein R$^a$ is as defined above;
—OCONR$^f$R$^a$, wherein R$^f$ and R$^a$ are as defined above;
—NR$^c$COOR$^d$, wherein R$^c$ and R$^d$ are as defined above;
—NR$^c$COR$^a$, wherein R$^c$ and R$^a$ are as defined above;
—CONR$^c$ wherein R$^c$ is as defined above;

n is an integer from 1 to 2;
m is 1;

D is situated in the ortho, meta or para position (preferably D is situated in the para position) and represents alkyl, acyl, aryl, alkylaryl, halogen, —CN, —NO$_2$, wherein the alkyl group is optionally substituted by R$^b$.
—OR$^a$, wherein R$^a$ is as defined above;
—OSO$_2$R$^d$, wherein R$^d$ is as defined above;
—OCONR$^a$R$^f$, wherein R$^a$ and R$^f$ are as defined above;
—NR$^c$COOR$^a$, wherein R$^c$ and R$^a$ are as defined above;
—NR$^c$COR$^a$, wherein R$^c$ and R$^a$ are as defined above;
—SO$_2$R$^d$, wherein R$^d$ is as defined above;
—SR$^c$, wherein R$^c$ is as defined above;
—CONR$^a$R$^c$, wherein R$^a$ and R$^c$ are as defined above;
—NR$^c$R$^a$, wherein R$^c$ and R$^a$ are as defined above;

D' is situated in the ortho, meta or para position (preferably D' is situated in the ortho or meta position) and represents hydrogen, alkyl, alkylaryl, halogen, —CN or —NO$_2$;
—OR$^h$, wherein R$^h$ is hydrogen or alkyl;

D" is situated in the ortho, meta or para position (preferably D" is situated in the ortho or meta position) and represents hydrogen, alkyl, alkylaryl, halogen, —CN or —NO$_2$;
—OR$^f$, wherein R$^f$ is as defined above.

Category A3: further preferred compounds of the present invention are those as defined within Category A2, but wherein A is situated in the meta or para position (preferably A is situated in the para position);

R is —OR$^a$, —SR$^a$, —SCOR$^a$ or —OSO$_2$R$^a$ wherein R$^a$ is hydrogen, alkyl or alkylaryl;

R$^2$ is cyano,
—OR$^a$ wherein R$^a$ is as defined above;
—NR$^c$COR$^a$ wherein R$^a$ and R$^c$ are as defined above;
—CONR$^c$R$^a$ wherein R$^a$ and R$^c$ are as defined above;

R$^1$, R$^3$ and R$^4$ are independently selected from hydrogen or alkyl (preferably both R$^1$, R$^3$ and R$^4$ are hydrogen);

D is situated in the ortho, meta or para position (preferably D is situated in the para position) and represents alkyl optionally substituted by R$^b$ or cyano;
—OR$^a$, wherein R$^a$ is as defined above.
—NR$^c$COR$^a$, wherein R$^a$ and R$^c$ are as defined above;
—CONHR$^c$R$^a$, wherein R$^a$ and R$^c$ are as defined above;
—NR$^c$COOR$^a$, wherein R$^c$, and R$^a$ are as defined above;
—OSO$_2$R$^a$, wherein R$^a$ is defined above;
—SO$_2$R$^d$, wherein R$^d$ is defined above;
—OCONR$^c$R$^a$, wherein R$^c$, and R$^a$ are as defined above;

D' is hydrogen.
D" is hydrogen.

Category A4: further preferred compounds of the present invention are those as defined within Category A3, but wherein A is situated in the para position;
R is —OH, —Oalkyl or —Oalkylaryl;
—SCOR$^a$ wherein R$^a$ is as defined above;
—OSO$_2$R$^d$ wherein R$^d$ is as defined above;
R$^1$ is hydrogen;
R$^2$ is —Oalkyl, preferably —Olower alkyl;
R$^3$ is hydrogen;
R$^4$ is hydrogen;
n is the integer 1;
D is is situated in the para position, and represents
—NR$^h$COOR$^d$, wherein R$^h$ represents hydrogen or alkyl.
CONR$^a$R$^c$ wherein R$^a$ and R$^c$ are as defined above;
—SO$_2$R$^d$ wherein R$^d$ is as defined above;
—OSO$_2$R$^d$ wherein R$^d$ is as defined above;
—CN;
—OR$^a$ wherein R$^a$ is as defined above;
—alkyl.

Category A5: further preferred compounds of the invention are those described in Category A4, but wherein R is
—OR$^a$ wherein R$^a$ is as defined above;
R$^2$ is —Oalkyl, preferably —Oloweralkyl;
D is
—NR$^b$COOR$^a$, wherein R$^b$ and R$^a$ are as defined above;
—CN;
—OSO$_2$R$^d$ wherein R$^d$ is as defined above;

Category A5: further preferred compounds of the invention are those described in examples 1 to 13.

Category A6: further preferred compounds of the present invention are compounds which are one of the possible enantiomers.

"Pharmaceutically acceptable salt", where such salts are possible, includes both pharmaceutically acceptable acid and base addition salts. A suitable pharmaceutically-acceptable salt of a compound of Formula I is, for example, an acid-addition salt of a compound of Formula I which is sufficiently basic, for example an acid-addition salt with an inorganic or organic acid such as hydrochloric, hydrobromic, sulphuric, trifluoroacetic, citric or maleic acid; or, for example a salt of a compound of Formula I which is sufficiently acidic, for example an alkali or alkaline earth metal salt such as a sodium, calcium or magnesium salt, or an ammonium salt, or a salt with an organic base such as methylamine, dimethylamine, trimethylamine, piperidine, morpholine or tris-(2-hydroxyethyl)amine.

In vivo hydrolysable esters of the compounds of Formula I are just one type of prodrug of the parent molecule. Other prodrugs of the parent molecule are envisaged such as amide prodrugs, and can be prepared by routine methodology well within the capabilities of someone skilled in the art. Prodrugs of the compound of Formula I are within the scope of the invention. Various prodrugs are known in the art. For examples of such prodrug derivatives, see:

a) Design of Prodrugs, edited by H. Bundgaard, (Elsevier, 1985) and Methods in Enzymology. 42: 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p.113–191 (1991);

c) H. Bundgaard, Advanced Drug Delivery Reviews, 8:1–38 (1992);

d) H. Bundgaard, et al., Journal of Pharmaceutical Sciences, 77:285 (1988); and e) N. Kakeya, et al., Chem Pharm Bull, 32:692 (1984).

The preferred examples of prodrugs include in vivo hydrolysable esters of a compound of the Formula I. Suitable pharmaceutically-acceptable esters for carboxy include $C_{1-8}$ alkyl esters, $C_{5-8}$ cycloalkyl esters, cyclic amine esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl wherein alkyl, cycloalkyl and cyclicamino groups are optionally substituted by, for example, phenyl, heterocyclcyl, alkyl, amino, alkylamino, dialkylamino, hydroxy, alkoxy, aryloxy or benzyloxy, and may be formed at any carboxy group in the compounds of this invention.

It will also be understood that certain compounds of the present invention may exist in solvated, for example hydrated, as well as unsolvated forms. It is to be understood that the present invention encompasses all such solvated forms.

When the substituent OR$^a$ represents an alkylaryl group, the preferred alkylaryl is benzyl.

Throughout the specification and the appended claims, a given chemical formula or name shall encompass all stereo and optical isomers and racemates thereof as well as mixtures in different proportions of the separate enantiomers, where such isomers and enantiomers exist, as well as pharmaceutically acceptable salts thereof and solvates thereof such as for instance hydrates. Isomers may be separated using conventional techniques, e.g. chromatography or fractional crystallisation. The enantiomers may be isolated by separation of racemate for example by fractional crystallisation, resolution or HPLC. The diastereomers may be isolated by separation of isomer mixtures for instance by fractional crystallisation, HPLC or flash chromatography. Alternatively the stereoisomers may be made by chiral synthesis from chiral starting materials under conditions which will not cause racemisation or epimerisation, or by derivatisation, with a chiral reagent. All stereoisomers are included within the scope of the invention.

The following definitions shall apply throughout the specification and the appended claims.

Unless otherwise stated or indicated, the term "alkyl" denotes either a straight or branched alkyl group having from 1 to 6 carbon atoms or a cyclic alkyl atom having from 3 to 6 carbon atoms, the alkyl being substituted or unsubstituted. The term "lower alkyl" denotes either a straight or branched alkyl group having from 1 to 3 carbon atoms or a cyclic alkyl having 3 carbon atoms, the alkyl being substituted or unsubstituted. Examples of said alkyl and lower alkyl include methyl, ethyl, n-propyl, isopropyl, n-butyl, iso-butyl, sec-butyl, t-butyl and straight- and branched-chain pentyl and hexyl as well as cyclopropyl, cyclobutyl, cyclopentyl and cyclohexyl. Preferred alkyl groups methyl, ethyl, propyl, isopropyl and tertiary butyl.

Unless otherwise stated or indicated, the term "alkoxy" denotes a group O-alkyl, wherein alkyl is as defined above.

Unless otherwise stated or indicated, the term "halogen" shall mean fluorine, chlorine, bromine or iodine, preferably fluorine.

Unless otherwise stated or indicated, the term "aryl" denotes a substituted or unsubstituted phenyl, furyl, thienyl or pyridyl group, or a fused ring system of any of these groups, such as naphthyl.

Unless otherwise stated or indicated, the term "substituted" denotes an alkyl or an aryl group as defined above which is substituted by one or more alkyl, alkoxy, halogen, amino, thiol, nitro, hydroxy, acyl, aryl or cyano groups.

Unless otherwise stated or indicated, the term "alkylaryl" denotes a

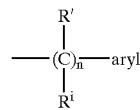

wherein n is an integer 1 to 6 and $R^r$ and $R^i$ are the same or different and each represents hydrogen or an alkyl or aryl group as defined above.

Unless otherwise stated or indicated, the term "acyl" denotes a group

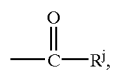

wherein $R^j$ is hydrogen, alkyl, alkoxy, aryl and alkylaryl as defined above.

Unless otherwise stated or indicated, the terms "alkenyl" and "alkynyl" denote a straight or branched, substituted or unsubstituted unsaturated hydrocarbon group having one or more double or triple bonds and having a maximum of 6 carbon atoms, preferably 3 carbon atoms.

Unless otherwise stated or indicated the term "protective group" denotes a protecting group as described in the standard text "Protecting groups in Organic Synthesis", 2nd Edition (1991) by Greene and Wuts. The protective group may also be a polymer resin such as Wang resin or 2-chlorotrityl chloride resin.

Methods of Preparation

The compounds of the invention may be prepared as outlined below according to any of the following methods. However, the invention is not limited to these methods, the compounds may also be prepared as described for structurally related compounds in the prior art.

A. The compounds of Formula I wherein R or $R^2$ is, where defined, $-OR^d$, $-SCOR^d$, $-SR^d$, $-OSO_2R^d$, $NR^cCOOR^a$, $NR^cCOR^a$, $-NR^aCONR^aR^k$ or $-NR^cSO_2R^d$ can be prepared by reaction of a compound of Formula I wherein the respective R or $R^2$ group is, for example, —OH, —SH or —$NHR^a$ with a suitable reagent, such as a thioate, a sulfonyl halide, an isocyanate, a chlorofortnate or an addition reagent for ether, such as alkylhalide or arylhalide. The reactions can be carried out in accordance with methods known to those skilled in the art, or as described in the examples. Suitable references are "Comprehensive Organic Transformations" R. C. Larock (VCH Publishers Inc.) 1989, p445–448, for the formation of alkyl or aryl ethers.

"Advanced Organic Chemistry" J. March ($4^{th}$ edition), John Wiley & Sons, 407–409, for the formation of thioethers, and 498–499, for the formation of sulfonates, 417–418, for the formation of amides, 411–413, for formation of amines.

B. The compounds of Formula I wherein R or $R^2$ is, where defined, $-SR^a$ or $-SCOR^a$ can be prepared by reaction of a compound of Formula I wherein the respective R or $R^2$ group is, for example, $-OSO_2R^a$ with a suitable reagent, respectively. $YSR^a$ or $YSCOR^a$ (wherein Y is a cation). Suitably the reaction is carried out in an inert solvent, such as DMF or methanol at room temprature with a suitable reducing agent, such as sodium borohydride, $LiAlH_4$, DIBAH or borane methylsulfide.

C. The compounds of Formula I, wherein X is 1, can be prepared by a reduction reaction of a compound of Formula II,

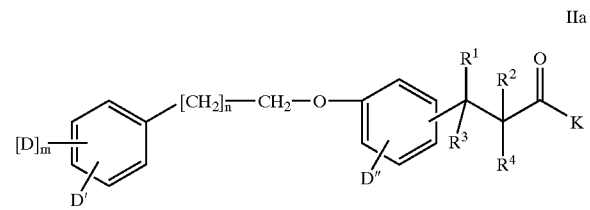

IIa

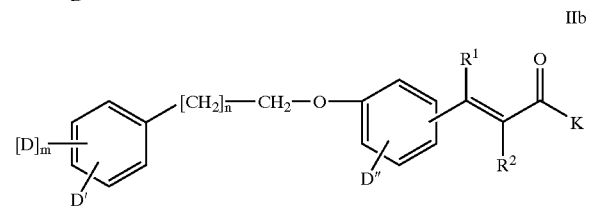

IIb wherein, K is $-OR^a$ or $-NR^aR^a$. The reaction is ideally carried out in an inert solvent, such as THF or methanol, and ideally at reduced temprature. Suitable reducing agents are those known to reduce carbonyl groups, such as, $NaBH_4$, DIBAH, $LiAlH_4$.

The compounds of formula IIa and IIb, wherein K is $-NR^aR^a$ may be prepared from the respective compounds of formula IIA and IEBK wherein K is $-OR^a$. The reactions can be carried out in accordane with methods known to those skilled in the art, or as described in the examples. Suitable references are found in Advanced Organic Chemistry" J. March ($4^{th}$ edition), John Wiley & Sons, 419–424.

The compounds of formula IIa can be prepared by an alkylation reaction with a compound of formula VIII

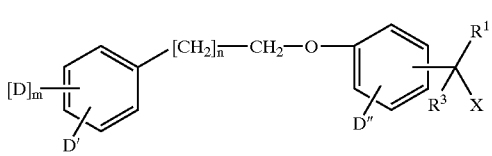

where X is a leaving group, such as halogen, a sulfonate or triflate, and a compound of formula IXa

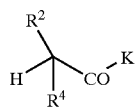

in which D, D', D", $R^1$, $R^2$, $R^3$, $R^4$, m, and n, are as defined in Category A and, if desired, followed by removal of any protective groups.

In the alkylation step the compound of Formula IXa is reacted with a compound of formula VIII in the presence of one or more bases such as potassium carbonate, triethylbenzylammonium chloride, sodium hydride, LDA, butyllithium or LHMDS and in a inert solvent such as acetonitrile, DMF or dichloromethane at a suitable temperature and time. The reaction can be carried out as described in the examples or by standard methods known in the literature (Synth. Comm. 19(788) 1167–1175 (1989)). C1. The compounds of Formula I wherein R, D or $R^2$ is cyano may be prepared by the dehydration of a compound of Formula I wherein the respective R, D or $R^2$ group is —$CONH_2$, such as compounds of Formula II where K is —$NH_2$. Ideally the reaction is carried out with an inert solvent, such as DMF or methanol at room temperature. The reagent is a suitable dehydrating agent such as trifluoroacetic anhydride. The reaction may be carried out according to analagous methods described in the literature, such as, Synthesis (1992) Falorni M. et al., 972–976 and J.Org.Chem. (1996), Heck M. P. et al., 61(19), 6486.

The compounds of Formula II can be prepared by a condensation reaction, such as a Knoevenagel or Wittig type reaction, of an aldehyde compound of the Formula III

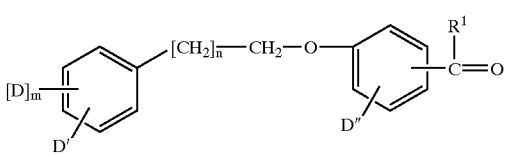

with a compound of the Formula IV or V

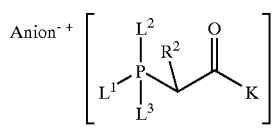

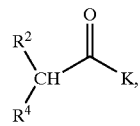

the anion is preferably a halogen such as chlorine or bromine, in which formulas D, D', D", m, n, $R^1$, $R^2$ and $R^4$ are as defined in Category A, X is 1, and $L^1=L^2=L^3$ are phenyl or $L^1=L^2$ are $OR^d$ (wherein $R^d$ is as defined in Category A) and $L^3$ is =O, followed by reduction of the double bond, if necessary to form the saturated compound of formula I, and removal of protective groups.

Approximately equimolar amounts of reactants are mixed in the presence of a base, such as sodium acetate, piperidine acetate, LDA or potassium tert-butoxide to provide the compound of formula I wherein A is the unsaturated moiety. This step may be carried out in the presence of an inert solvent or in the absence of solvent in which case the temperature should be sufficiently high to cause at least partial melting of the reaction mixture, a preferred such temperature is in the range of 100° C. to 250° C.

Where $R^4$ is not hydrogen it is necessary to add a dehydroxylating agent in order to remove the formed —OH at the β carbon. Suitable reaction conditions and reagents are described in Synthetic Communications Smonou I et al., (1988) 18, 833, and Synthesis Olag G. Et al., (1991) 407, and J.Heterocyclic Chemistry Georgiadis, M. P. Etal., (1991) 28(3), 599–604, and Synth. Commun. Majeticj, G. et al. (1993), 23(16), 2331–2335, and Bioorg. Med. Chem. Lett. (1998) 8(2), 175–178.

Sometimes it is necessary, when $R^4$ is H, to add a dehydrating agent such as p-toluenesulfonic acid in order to achieve the formation of the double bond. In a typical such reaction the starting material of formula III and the compound of formula IV are combined in approximately equimolar amounts and molar excess, preferably 1–5 fold, of anhydrous sodium acetate and the mixture is heated until it melts if necessary under vacuum. The compound of formula IIb can then be isolated by mixing with water and acetone, followed by filtration of the formed precipitate. The crude product can be purified if desired, e.g. by recrystallization or by standard chromatographic methods.

This reaction can also be performed conveniently in a solvent such as toluene in the presence of piperidine acetate. The reaction mixture is refluxed in a Dean-Stark apparatus to remove water. The solution is then cooled and the olefin product isolated and purified,
by standard methods.

The reaction can also be performed by mixing the starting material and the compound of formula V in dry THF, slowly adding potassium tert-butoxide at −20° C. and quenching the reaction with acetic acid. The crude product is isolated and then dissolved in toluene and refluxed with p-toluenesulfonic acid in a Dean-Stark apparatus to remove the water. The product is then isolated and purified, by standard methods.

The reaction can also be performed in the presence of titanium (IV) chloride and pyridine in an inert solvent, such as chloroform.

The condensation step could also be performed as a Wittig-type reaction (cf. with a compound of formula IV Comprehensive Organic Synthesis vol. 1 p. 755–781 Pergamon Press).

Approximately equimolar amounts of reactants III and IV, are mixed in the presence of a base such as tetramethylguanidine or potassium carbonate in a 1–5 fold molar excess. This reaction may be carried out in the presence of an inert solvent such as dichloromethane or isopropanol at a suitable temperature (−10° C. to +60° C.) and at a time long enough.

The compound of the formula III is prepared by coupling a compound of the formula VI

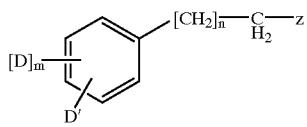

VI with a compound of the formula VII

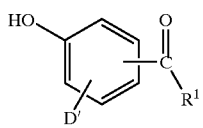

VII in which formulas D, D', D", $R^1$, m and n are as defined in Category A, at, for example alkylation conditions or by a Mitsunobu reaction (Tsunoda, Tetr. Lett. 34, 1639–42 (1993), when necessary followed by modifications of the D-groups as described in the experimental section.

The group Z can be —OH or a leaving group, such as halogen, sulfonate or triflate. The alkylation reaction and the Mitsunobu reaction can be carried out as described below or as in the experimental section.

The compounds of formula IV, V, VI and VII are either commercially available or can be prepared by standard procedures known to anyone skilled in the art from commercially available starting materials or by analagous procedures described in this application.

D. The reduction of the olefin version of the compound of formula I to the saturated version of a compound of formula I may be carried out by using a wide variety of reducing methods known to reduce carbon—carbon double bonds, such as catalytic hydrogenation in the presence of an appropriate catalyst, magnesium or sodium amalgam in a lower alcohol such as methanol, or hydrogen transfer reagents such as diethyl-2,5-dimethyl-1,4-dihydropyridine-3,5-dicarboxylate.

The catalytic hydrogenation can be conducted in alcohol, cellosolves, protic polar organic solvents, ethers, lower aliphatic acids, and particularly in methanol, ethanol, methoxyethanol, dimethylformamide, tetrahydrofuran, dioxane, dimethoxyethane, ethyl acetate or acetic acid, either used alone or in mixture. Examples of the catalyst used include palladium black, palladium on activated charcoal, platinum oxide or Wilkinson's catalyst. The reaction can proceed at different temperatures and pressures depending on the reactivity of the aimed reaction.

In case of hydrogen transfer reaction with diethyl-2,5-dimethyl-1,4-dihydropyridine-3,5-dicarboxylate, equimolar amounts of reactants are mixed and the mixture is warmed to melting (140° C.–250° C.) under inert atmosphere or under vacuum.

E. The compounds of the invention of formula I can be prepared by an alkylation reaction with a compound of formula VIII

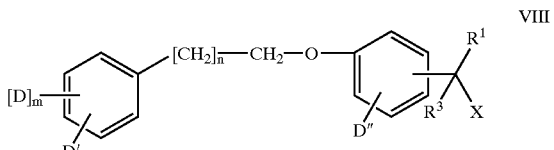

VIII where X is a leaving group, such as halogen, a sulfonate or triflate, and a compound of formula IXb

IXb in which formulas D, $D^1$ $R^1$, $R^2$, $R^3$, $R^4$, n, x, and D", are as defined in Category A and, if desired, followed by removal of any protective groups.

In the alkylation step the compound of Formula IX is reacted with a compound of formula VIII in the presence of one or more bases such as potassium carbonate, triethylbenzylammonium chloride, sodium hydride, LDA, butyllithium or LHMDS and in a inert solvent such as acetonitrile, DMF or dichloromethane at a suitable temperature and time. The reaction can be carried out as described in the examples or by standard methods known in the literature (Synth. Comm. 19(788) 1167–1175 (1989)).

The compound of Formula VIII can be prepared from an alcohol of formula X

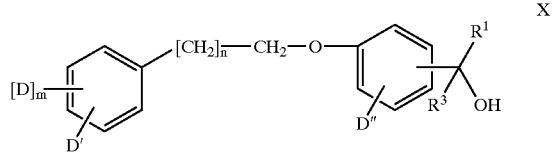

X wherein D, D', D" $R^1$, $R^3$ and n are as defined in Category A using standard methods.

The compound of Formula X can be prepared from a compound of Formula III either by reduction with a reducing agent known to convert a carbonyl group to a hydroxyl group such as lithium borohydride or sodium borohydride or by reaction with an organometallic compound such as an organolithium or a Grignard reagent by standard methods.

F. The compounds of the invention of Formula I can be prepared by reaction of a compound of formula VI with a compound of the Formula XI

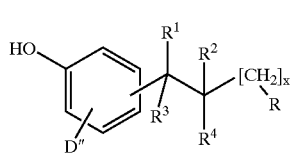

XI in which formulas D, D', D", $R^1$, $R^2$, $R^3$, $R^4$, m,n, x and R are as defined in Category A, in a similar reaction as described above, additional protective groups may be necessary.

The compound of Formula XI can be prepared in accordance to method C from commercially available starting materials and compounds of formula IV or V.

The reaction is carried out according to standard procedure for an alkylation or Mitsunobu reaction.

F1. In an alkylation reaction the leaving group Z of the compound of formula VI can be a sulfonate such as mesylate, nosylate, tosylate, or a halogen, such as bromine or iodine. The compounds of Formula VI and XI, in approximately equimolar amounts or with an excess of one of the compounds, are heated to reflux temperature in an inert solvent, such as isopropanol or acetonitrile, in the presence of a base, such as potassium carbonate or cesium carbonate.

The mixture is refluxed for the necessary time, typically between 0.5 h to 24 h, the work up procedure usually include filtration, for removal of solid salt, evaporation and extraction with water and an organic solvent such as dichloromethane, ethyl acetate, or diethyl ether.

The crude product is purified if desired e.g. by recrystallization or by standard chromatographic methods.

F2. The Mitsunobu reaction can be carried out according to standard methods. In a typical Mitsunobu reaction a compound of Formula VI, wherein the group F of the compound of Formula VI is a hydroxyl group, and a compound of formula XI are mixed, in approximately equimolar amounts or with an excess of one of the compounds, in an inert solvent, such as chloroform, dichloromethane, or THF. A slight molar excess of an azodicarboxylate, (1–4 equivalents) such as DEAD or ADDP and a phosphine (1–4 equivalents), such as tributylphosphine or triphenylphosphine are added and the reaction mixture is stirred at a temperature high enough, for example room temperature, and a time long enough (1–24 hours) to obtain the crude product, which can be worked up according to standard literature methods and if desired purified, e.g. by standard chromatographic methods.

G. The compounds of the invention of Formula I wherein D is —OSO$_2$R$^d$, —SR$^c$, —OCONR$^f$R$^a$, —NR$^c$COOR$^a$, —NR$^c$COR$^a$, NR$^c$R$^d$, —NR$^c$CONR$^a$R$^d$, NR$^c$SO$_2$R$^d$ and —NR$^c$CSNR$^a$R$^k$, wherein R$^a$, R$^c$, R$^d$, R$^f$ and R$^k$ are as defined in Category A, can be prepared by reacting a compound of Formula XI

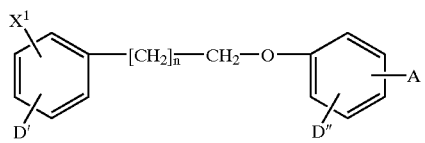

XII wherein D', D", n and A are as defined in Category A and X$^1$=—OH, —SH or —NR$^c$H, with a suitable reagent, such as a sulfonylhalide, isocyanate, acylhalide, chloroformate, anhydride or an alkylhalide in an inert solvent such as dichloromethane or toluene and when necessary in the presence of a base, such as triethylamine or pyridine and eventually followed by removal of protective groups.

The reaction can be carried out in accordance with methods known to those skilled in the art.

H. The compounds of the invention of Formula I where D is —SO$_2$R$^d$ or —SOR$^d$, wherein R$^d$ is as defined in Category A, can be prepared by oxidizing a compound of formula

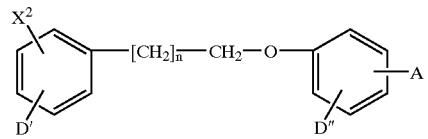

XIV wherein D', D", n and A are as defined in Category A and X$^2$ is —SOR$^d$ or —SR$^d$, wherein R$^d$ is as defined in Category A, with oxidizing agents such as m-chloroperoxybenzoic acid or hydrogen peroxide in an inert solvent such as dichloromethane eventually followed by removal of protective groups. Compounds of Formula XIV where R contains a —S— or —SO— group should not be used unless oxidation of such groups is required.

The reactions can be carried out according to standard procedures or as described in the experimental section.

The compounds of the invention may be isolated from their reaction mixtures using conventional techniques.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

In any of the preceding methods of preparation A—H, where necessary, hydroxy, amino or other reactive groups may be protected using a protecting group, as described in the standard text "Protective groups in Organic Synthesis", 2$^{nd}$ Edition (1991) by Greene and Wuts. The protecting group may also be a resin, such as Wang resin or 2-chlorotrityl chloride resin. The protection and deprotection of functional groups may take place before or after any of the reaction steps described hereinbefore. Protecting groups may be removed in accordance to techniques which are well known to those skilled in the art.

The expression "inert solvent" refers to a solvent which does not react with the starting materials, reagents, intermediates or products in a manner which adversely affects the yield of the desired product.

Pharmaceutical Preparations

The compounds of the invention will normally be administered via the oral, parenteral, intravenous, intramuscular, subcutaneous or in other injectable ways; buccal, rectal, vaginal, transdermal and/or nasal route and/or via inhalation, in the form of pharmaceutical preparations comprising the active ingredient either as a free acid, or a pharmaceutically acceptable organic or inorganic base addition salt, in a pharmaceutically acceptable dosage form. Depending upon the disorder and patient to be treated and the route of administration, the compositions may be administered at varying doses.

The compounds of the invention may also be combined with other therapeutic agents which are useful in the treatment of disorders associated with the development and progress of atherosclerosis such as hypertension, hyperlipidemias, dyslipidemias, diabetes and obesity. Suitable daily doses of the compounds of the invention in the therapeutic treatment of humans are about 0.001–10 mg/kg body weight, preferably 0.01–1 mg/kg body weight.

According to a further aspect of the invention there is also provided a pharmaceutical formulation including any of the compounds of the invention, or pharmaceutically acceptable derivatives thereof, in admixture with pharmaceutically acceptable adjuvants, diluents and/or carriers.

Pharmacological Properties

The present compounds of formula (I) are useful for the prophylaxis and/or treatment of clinical conditions associated with reduced sensitivity to insulin (insulin resistance) and associated metabolic disorders. These clinical conditions will include, but will not be limited to, abdominal obesity, arterial hypertension, hyperinsulinaemia, hyperglycaemia, type 2 diabetes mellitus and the dyslipidaemia characteristically appearing with insulin resistance. This dyslipidaemia, also known as the atherogenic lipoprotein profile, phenotype B, is characterised by moderately elevated non-esterified fatty acids, elevated very low density lipoproteins (VLDL) triglyceride rich particles, low high density lipoproteins (HDL) particle levels cholesterol and the presence of small, dense, low density lipoprotein (LDL) particles. Treatment with the present compounds is expected to lower the cardiovascular morbidity and mortality associated with atherosclerosis. These cardiovascular disease conditions include macro-angiophaties causing myocardial infarction, cerebrovascular disease and peripheral arterial insufficiency of the lower extremities. Because of their insulin sensitizing effect the compounds of formula I are also expected to prevent or delay the development of type 2 diabetes and thus reduce the progress of clinical conditions associated with chronic hyperglycaemia in diabetes type 1 such as the micro-angiophaties causing renal disease, retinal damage and peripheral vascular disease of the lower limbs. Furthermore the compounds may be useful in treatment of various conditions outside the cardiovascular system associated with insulin resistance like polycystic ovarian syndrome.

WORKING EXAMPLES $^1$H NMR and $^{13}$C NMR measurements were performed on a Varan Mercury 300 or Varian UNITY plus 400, 500 or 600 spectrometers, operating at $^1$H frequencies of 300, 400, 500 and 600 MHz, respectively, and at $^{13}$C frequencies of 75, 100, 125 and 150 MHz, respectively. Measurements were made on the delta scale ($\delta$).

Unless otherwise stated, chemical shifts are given in ppm with the solvent as internal standard.

| Abbreviations | |
|---|---|
| IRS | insulin resistance syndrome |
| LDA | lithium diisopropylamide |
| LHMDS | lithium hexamethyldisilylamine |
| DMF | dimethylformamide |
| DEAD | diethyl azodicarboxylate |
| ADDP | azodicarbonyl dipiperidine |
| EDC | 1-(3-dimethylaminopropyl)-3-ethylcarbodiimide |
| DCC | dicyclohexylcarbodiimide |
| HBTU | O-benzotriazol-1-yl-N,N,N',N'-tetramethyluronium hexafluorophosphate |
| TBTU | O-benzotriazol-1-yl-N,N,N',N'-tetramethyluronium tetrafluoroborate |
| PyBop | benzotriazole-1-yl-oxy-tris-pyrolidino-phosphonium hexafluorophosphate |
| TEA | triethylamine |
| DIPEA | diisopropylethylamine |
| TLC | thin layer chromatography |
| THF | tetrahydrofuran |
| HO-Su | N-hydroxy succinimide |
| Pd/C | palladium on charcoal |
| HOBtxH$_2$O | 1-hydroxybenzotriazole-hydrate |

| -continued | |
|---|---|
| Abbreviations | |
| DIBAH | diisobutylaluminium hydride |
| DMSO | dimethyl sulfoxide |
| t | triplet |
| s | singlet |
| d | doublet |
| q | quartet |
| qvint | quintet |
| m | multiplet |
| br | broad |
| bs | broad singlet |
| dm | doublet of multiplet |
| bt | broad triplet |
| dd | doublet of doublet |

Example 1

3-[4-(2-{4-(Cyanophenyl} ethoxy)phenyl]-2-ethoxypropanol

Ethyl 3-{4-[2-(4-cyanophenyl)ethoxy]phenyl}-2-ethoxypropanoate (0.666 g, 1.81 mmol) was dissolved in dry THF (13 ml) and methanol (0.5 ml) and cooled to −10° C.—20° C. Sodium borohydride (0.119 g, 3.14 mmol) was added. After stirring for 6 hours the temperature was raised to room temperature. After stirring for another 25 hours water was added, the product was extracted with diethylether, washed with water and dried (sodium sulfate). Evaporation in vacuo of the solvent gave 0.573 g (yield 97%) of the desired product.

$^1$H-NMR (400 MHz; CDCl$_3$): 1.18 (t, 3H, J=7 Hz), 2.07 (bs 1 OH), 2.65–2.72 (m, 1H), 2.77–2.84 (m, 1H), 3.14 (t, 2H, J=6.6 Hz), 3.4–3.46 (m, 1H), 3.46–3.63 (m, 4H), 4.18 (t, 2H, J=6.6 Hz), 6.8 (dm, 2H, J=8.6 Hz, unresolved), 7.11 (dm, 2H, J=8.6 Hz, unresolved), 7.4 (dm, 2H, J=8.1 Hz, unresolved), 7.60 (dm, 2H, J=8.1 Hz, unresolved).

$^{13}$C-NMR (100 MHz; CDCl$_3$): 15.4, 35.8, 36.4, 63.5, 65.1, 67.6, 81.0, 110.3, 114.4, 118.8, 129.7, 130.3, 130.6, 132.1, 144.2, 156.9.

Starting Material (a) Ethyl 3-{4-[2-(4-cyanophenyl)ethoxy]phenyl}-2-ethoxypropanoate Ethyl 2-ethoxy-3-(4-hydroxyphenyl) propanoate, described in example 3(b)(6.62 g; 27.78 mmole) and p-cyanophenethyl alcohol (2.73 g; 18.52 mmole) were mixed in dichloromethane (85 ml). ADDP (7.01 g; 27.78 mmole) was added followed by addition of triphenylphosphine (5.83 g; 22.23 mmole). The reaction was interrupted after 2 hours. Triphenylphosphine oxide formed in the reaction was filtered off and the filtrate was evaporated. The residue was purified bychromatography on silica gel using first dichloromethane and then petroleum ether:diethyl ether as eluants giving a mixture of product and starting material which was dissolved in ethyl acetate and washed with sodium hydroxide (1 N). The organic phase was washed with water, dried (sodium sulfate), filtered and the solvent was evaporated to give 4.23 g (yield 62%) of the desired product.

$^1$H-NMR (400 MHz; CDCl$_3$): 1.16 (t, 3H, J=7 Hz), 1.23 (t, 3H, J=7 Hz), 2.93–2.97 (m, 2H), 3.14 (t, 2H, J=6.4 Hz), 3.3–3.4 (m, 1H), 3.56–3.65 (m, 3H), 3.94–3.99 (m, 1H), 4.14–4.26 (m, 4H), 6.8 (dm, 2H, J=8.6 Hz, unresolved), 7.15 (dm, 2H, J=8.6 Hz, unresolved), 7.4 (dm, 2H, J=8.3 Hz, unresolved), 7.60 (dm, 2H, J=8.3 Hz, unresolved).

$^{13}$C-NMR (100 Mz; CDCl$_3$): 14.1, 15.0, 35.8, 38.4, 60.7, 66.1, 67.5, 80.2, 110.3, 114.2, 118.8, 129.66, 129.74, 130.4, 132.1, 144.2, 157.2, 172.4.

Example 2

2-Ethoxy-3-{3-[3-(4-methylsulfonyloxyphenyl)propoxy]phenyl}propanol

The compound was synthesised in an analogous method to Example 1 using ethyl 2-ethoxy-3-{3-[3-(4-methylsulfonyloxyphenyl)propoxy]phenyl}propanoate (0.642 g, 1.42 mmol) and sodium borohydride (93.26 mg, 2.47 mmol). The reaction was quenched after 28 hours to give 0.574 g (yield 99%) of the desired product.

$^1$H-NMR (500 MHz; CDCl$_3$): 1.23 (t, 3H, J=7.0 Hz), 2.02(bt, 1 OH, J=6.2 Hz), 2.13 (qvint, 2H, J=6.9 Hz), 2.72–2.78 (m, 1H), 2.85–2.93 (m, 3H), 3.17 (s, 3H), 3.46–3.70 (m, 5H), 4.0 (t, 2H, J=6.1 HZ), 6.77–6.81 (m, 2H), 6.84 (dm, 1H, J=7.8 Hz, unresolved), 7.21–7.26 (m, 3H), 7.28–7.32 (m, 2H).

$^{13}$C-NMR (125 MHz; CDCl$_3$): 15.5, 30.8, 31.6, 37.2, 37.5, 63.7, 65.2, 66.5, 80.9, 112.2, 115.7, 121.8, 121.9, 129.4, 130.0, 139.8, 141.0, 147.4, 158.9.

Starting Material (a) 3-(3-Benzyloxyphenyl)-2-ethoxyacrylic acid ethyl ester

Tetramethylguanidine (6.5 g; 56.6 mmole) was slowly added to a solution of 3-benzyloxybenzaldehyde (11.7 g; 55 mmole) and (1,2-diethoxy-2-oxoethyl)(triphenyl) phosphonium chloride (20.1 g; 46.8 mmole) in dichloromethane (200 ml) at 0° C. After stirring at room temperature overnight the solvent was evaporated in vacuo. Diethyl ether was added and insoluble material was filtered off. The filtrate was washed with sodium bicarbonate solution, dried (magnesium sulfate), filtered and the solvent was evaporated in vacuo. The residue was purified by chromatography on silica gel using THY (0.5%) in dichloromethane as eluant. The remaining aldehyde was removed by stirring with sodium bisulfite in water and diethyl ether for 2 days. The phases were separated and the organic phase was evaporated in vacuo to give 10.5 g (yield 69%) of the desired product.

$^1$H-NMR (300 MHz; CDCl$_3$): 1,4 (m, 6H), 4.02 (q, 2H), 4.32 (q, 2H), 5.12 (s, 2H), 6.97 (unresolved, 2H), 7.3–7.5 (m, 7H), 7.7 (unresolved, 1H).

$^{13}$C-NMR (75 Mz; CDCl$_3$): 14.3, 15.6,61.2, 67.7, 69.9, 115.6, 116.1, 123.2, 123.7, 127.4, 128.0, 128.6, 129.4, 135.0, 137.0, 144.9, 158.8, 164.6.

(b) Ethyl 2-ethoxy-3-(3-hydroxyphenyl)propanoate

Compound (a) (10.4 g; 31.8 mmole) was hydrogenated at atmospheric pressure in ethyl acetate using Pd/C (dry, 10%) as a catalyst. The reaction mixture was filtered through celite and the solvent was evaporated in vacuo. The starting material was not completely consumed, therefore the hydrogenation was repeated to give 7 g (yield 92%) of the desired product.

$^1$H-NMR (300 MHz; CDCl$_3$): 1.15 (t, 3H), 1.22 (t, 3H), 2.95 (m, 2H), 3.4 (m, 1H), 3,6 (m, 1H), 4.05 (m, 1H), 4.15 (q, 2H).

$^{13}$C-NMR (75 MHz; CDCl$_3$): 14.1,15.0,39.2, 61.2, 66.4, 80.2, 113.9, 116.5, 121.2,129.4, 137.2, 138.5, 156.0.

(c) 3-(4-Methylsulfonyloxyphenyl)propylmethanesulfonate 3-(4-Methylsulfonyloxyphenyl)propylmethanesulfonate was synthesized using the same method as in Example 8 from 3-(4-hydroxyphenyl)-1-propanol.

$^1$H-NMR (400 MHz; CDCl$_3$): 2.1 (q, 2H), 2.8 (t, 2H), 3.0 (s, 3H), 3.15 (s, 3H), 4.25 (t, 2H), 7.23–7.27 (m, 4H).

$^{13}$C-NMR (100 MHz; CDCl$_3$): 31.7,32.1, 38.4,38.5, 69.8, 123.2, 131.1, 140.9,148.7.

(d) Ethyl 2-ethoxy-3-{3-[3-(4-methylsulfonyloxyphenyl)propoxy]phenyl}propanoate

Compound (c) (1.905 g; 6.18 mmole) was dissolved in acetonitrile (13 ml) and added dropwise to a mixture of ethyl 2-ethoxy-3-(3-hydroxyphenyl)-propanoate (1.47 g; 6.18 mmole) and potassium carbonate (2.56 g; 18.54 mmole) in acetonitrile (15 ml). The mixture was refluxed for 5 hours, then the solvent was evaporated in vacuo and water was added. The mixture was extracted twice with dichloromethane, dried (sodium sulfate), filtered and the solvent was evaporated in vacuo. Purification by chromatography on silica gel using diethyl ether/petroleum ether (gradient 33% to 100% diethyl ether) gave 1.80 g (yield 65%) of the desired product.

$^1$H-NMR (400 MHz; CDCl$_3$): 1.17 (t, 3H, J=7 Hz), 1.24 (t, 3H, J=7.3 Hz), 2.05–2.14 (m, 2H), 2.84 (t, 2H, J=7.5 Hz), 2.97–3.01, (m, 2H), 3.14 (s, 3H), 3.33–3.42 (m, 1H), 3.58–3.66 (m, 1H), 3.96 (t, 2H, J=6 Hz), 4.0–4.05 (m, 1H), 4.15–4.23 (m, 2H), 6.74–6.87 (m, 3H), 7.17–7.24 (m, 3H), 7.25–7.30 (m, 2H).

$^{13}$C-NMR (100 MHz; CDCl$_3$): 14.2, 15.0, 30.7, 31.6, 37.2, 39.4, 60.8, 66.2, 66.5, 80.1, 112.8, 115.6, 121.8, 121.9, 129.2, 130.0, 138.8, 141.0, 147.4, 158.8, 172.4.

Example 3

3-{4-[2-(4-tert-Butoxycarbonylaminophenyl)ethoxy]phenyl}-2-ethoxypropanol

The compound was synthesised in an analogous method to Example 1 using ethyl 3-{4-[2-(4-tert-butoxycarbonylaminophenyl)ethoxy]phenyl)-2-ethoxypropanoate (0.994 g, 2.172 mmol) and sodium borohydride (0.164 g, 4.34 mmol). The reaction was quenched after 21 hours and the product was extracted with ethyl acetate. The organic phase was washed with sodium sulfite and brine, dried (sodium sulfate), filtered and solvent was evaporated in vacuo. The crude product was purified by chromatography on silica gel using heptane:ethyl acetate (gradient 2:1 tol:2) as eluants to give 0.5 g (yield 55%) of the desired product.

$^1$H-NMR (400 MHz; CDCl$_3$): 1.19 (t, 3H, J=7.1 Hz), 1.53 (s, 9H), 1.98 (dd, 1 OH, J=5.4 Hz and 7.3 Hz), 2.68 (dd, 1H, J=7 Hz and 13.7 Hz), 2.82 (dd, 1H, J=5.9 Hz and 13.7 Hz), 3.04 (t, 2H, J=7.1 Hz), 3.40–3.48 (m, 1H), 3.48–3.65 (m, 4H), 4.12 (t, 2H, 3=7.1 Hz), 6.46 (bs, 1 NH), 6.82 (dm, 2H, J=8.8 Hz, unresolved), 7.10 (dm, 2H, J=8.8 Hz, unresolved), 7,21(dm, 2H, J=8.8 Hz, unresolved), 7.31(dm, 2H, J=8.3 Hz, unresolved).

$^{13}$C-NMR (100 MHz; CD$_3$OD): 15.8, 28.7, 36.1, 37.8, 64.3, 66.4, 69.9, 80.7, 83.1, 115.4, 120.1, 130.3, 131.4, 132.1, 134.2, 138.8, 155.4, 158.8.

Starting Material (a) 3-(4-Benzyloxyphenyl)-2-ethoxyacrylic acid ethyl ester

Tetramethylguanidine (42.3 g; 0.37 mole) was slowly added to a solution of 4-benzyloxybenzaldehyde (75.6 g; 0.36 mole) and (1,2-diethoxy-2-oxoethyl) (triphenyl) phosphonium chloride (130.7 g; 0.304 mole) dissolved in chloroform (800 ml) at 0° C. After stirring at room temperature over night, the solvent was evaporated in vacuo. The residue was dissolved in diethyl ether, insoluble material was filtered off and the filtrate was washed with sodium bicarbonate and dried (magnesium sulfate). The procedure was repeated once and thereafter the crude product was stirred over night with a sodium bisulfite saturated water solution. The solid material was filtered off, the product was extracted with diethyl ether, dried (magnesium sulfate) and the solvent was evaporated in vacuo to give 85 g (yield 73%) of the desired product.

$^1$H-NMR (300 MHz; CDCl$_3$): 1.35 (m, 6H), 4.0 (q, 2H), 4.3 (q, 2H), 5.05 (s, 2H), 6.95 (s+m unresolved, 1+3H), 7.3–7.45 (m, 5H), 7.75 (d, 2H).

¹³C-NMR (125 MHz; CDCl₃): d 14.4, 15.6, 61.0, 67.5, 70.0, 114.8, 124.0, 126.7, 127.5, 128.1, 128.6, 131.7, 136.7, 143.1, 159.2, 165.0.

(b) Ethyl 2-ethoxy-3-(4-hydroxyphenyl)propanoate

Compound (a) (62 g; 0.19 mole) was hydrogenated in ethyl acetate (400 ml) at atmospheric pressure using Pd/C (10%) as catalyst. The mixture was filtered through celite and evaporated in vacuo to give 45.6 g (yield 100%) of the desired product.

¹H-NMR (600 MHz; CDCl₃): 1.17 (t, 3H, J=7 Hz), 1.23 (t, 3H, J=7 Hz), 2.95 (d, 2H, J=6.6 Hz), 3.35–3.42 (m, 1H), 3.58–3.64 (m, 1H), 4.0 (t, 1H, J=6.6 Hz), 4.17 (q, 2H, J=7 Hz), 5.97 (s, 1 OH), 6.74 (dm, 2H, J=8.5 Hz, unresolved), 7.08 (dm, 2H, J=8.5 Hz, unresolved).

¹³C-NMR (125 MHz; CDCl₃): 14.0, 14.8, 38.3, 61.0, 66.1, 80.3, 115.1, 128.2, 130.3, 154.8, 173.0.

(c) 4-(2-Hydroxyethyl)phenylcarbamic acid tert-butyl ester

Di-tert-butyl dicarbonate (7.95 g; 36 mmole) was added to a mixture of p-aminophenethyl alcohol (5 g; 36 mmole) in THF at 0° C. After stirring at room temperature over night, the solvent was evaporated in vacuo to give 8 g (yield 94%) of the desired product.

¹H-NMR (400 MHz; DMSO-d₆): 1,5 (s, 9H), 2,65 (dd, 2H), 3,55 (dd, 2H), 4,6 (s, br, 1 OH), 7,1 (unresolved, 2H), 7,35 (unresolved, 2H), 9,1 (s, 1 NH).

¹³C-NMR (100 MHz; DMSO-d₆): 28.3, 38.6, 62.5, 78.9, 118.3, 129.1, 133.2, 136.6, 153.0.

(d) Ethyl 3-{4-[2-(4-tert-butoxycarbonylaminophenyl)ethoxy]phenyl}-2-ethoxypropanoate Compound (c) (1.03 g; 4.34 mmole) and (b) (1.03 g; 4.34 mmole) were dissolved in dichloromethane under argon at room temperature. Azodicarbonyl dipiperidine (1.65 g; 6.5 mmole) and thereafter triphenylphosphine (1.37 g; 5.2 mmole) were added. After stirring at room temperature for 6 hours the solvent was evaporated in vacuo. Purification by chromatography on silica gel using heptane:ethyl acetate (2:1) as eluant gave 1.78 g (yield 89%) of the desired product.

¹H-NMR (400 MHz; CDCl₃): 1.17 (t, 3H, J=7 Hz), 1.23 (t, 3H, J=7 Hz), 1.53 (s, 9H), 2.94–2.97 (m, 2H), 3.03 (t, 2H, J=7.1 Hz), 3.31–3.40 (m, 1H), 3.56–3.65 (m, 1H), 3.95–4.0 (m, 1H), 4.11 (t, 2H, J=7.1 Hz), 4.17 (q, 2H, J=7 Hz), 6.60 (s, 1NH), 6.81 (dm, 2H, J=8.3 Hz, unresolved), 7.15 (dm, 2H, J=8.3 Hz, unresolved), 7.20 (dm, 2H, J=8.3 Hz, unresolved), 7.31 (dm, 2H, J=8.3 Hz, unresolved).

¹³C-NMR (100 MHz; CDCl₃): 14.1, 15.0, 28.3, 35.0, 38.4, 60.7, 66.1, 68.6, 80.26, 80.32, 114.3, 118.7, 128.2, 129.4, 130.3, 132.8, 136.7, 152.8, 157.5, 172.4.

Example 3a

3-{4-[2-(4-tert-Butoxycarbonylaminophenyl)ethoxy]phenyl}-(2R)-2-ethoxypropanol

The racemate of Example 3 was separated using chiral preparative HPLC (Chiralpak AD 250×50 mm) using heptane and isopropanol (1:1) as mobil phase giving the desired product as a pure enantiomer.

¹H-NMR (300 MHz; CDCl₃): 1.19 (t, 3H), 1.54 (s, 9H), 2.30 (—OH), 2.64–2.88 (m, 2H), 3.04 (t, 2H), 3.38–3.70 (m, 5H), 4.12 (t, 2H), 6.72 (—NH), 6.83 (d, 2H), 7.12 (d, 2H), 7.21 (d, 2H), 7.33 (d, 2H)

¹³C-NMR (75 MHz; CDCl₃): 15.9, 28.7, 30.1, 35.5, 36.9, 64.0, 65.6, 69.1, 80.7, 81.6, 114.8, 119.1, 129.7, 130.5, 133.1, 137.1, 157.6

Example 3b

3-{4-[2-(4-tert-Butoxycarbonylaminophenyl)ethoxy]phenyl}-(2S)-2-ethoxypropanol

The racemate of Example 3 was separated using chiral preparative HPLC (Chiralpak AD 250×50 mm) using heptane and isopropanol (1:1) as mobil phase giving the desired product as a pure enantiomer.

¹H-NMR (300 MHz; CDCl₃): 1.19 (t, 3H), 1.54 (s, 9H), 2.30 (—OH), 2.64–2.88 (m, 2H), 3.04 (t, 2H), 3.38–3.70 (m, 5H), 4.12 (t, 2H), 6.72 (—NH), 6.83 (d, 2H), 7.12 (d, 2H), 7.21 (d, 2H), 7.33 (d, 2H)

¹³C-NMR (75 MHz; CDCl₃): 15.9, 28.7, 30.1, 35.5, 36.9, 64.0, 65.6, 69.1, 80.7, 81.6, 114.8, 119.1, 129.7, 130.5, 133.1, 137.1, 157.6

Example 4

3-[4-(2-{4-tert-Butoxycarbonylaminophenyl}ethoxy)phenyl]-2-ethoxypropyl methanesulfonate Example 3 (0.81 g, 2.0 mmole) was dissolved in dry THF (10 ml) and cooled to −20° C. Triethylamine (0.24 g, 2.4 mmole) was added dropwise to the mixture and after 10 minutes stirring methanesulfonylchloride (0.27 g, 2.4 mmole) was added. After 4 hours it was checked with HPLC that all the starting material was consumed. Hydrochloric acid (5 ml) was added, the THF was evaporated and the residue extracted three times with ethyl acetate. The organic phase was dried with magnesium sulfate and evaporated giving 1.0 g (99% yield) of the desired product.

¹H-NMR (500 MHz; CDCl₃): 1.15 (t, 3H), 1.51 (s, 9H), 2.77 (m, 2H), 2.99–3.04 (t, 2H), 3.02 (s, 3H), 3.44–3.62 (m, 2H), 3.63–3.70 (m, 1H), 4.03–4.25 (m, 4H), 6.66 (—NH), 6.81 (d, 2H), 7.10 (d, 2H), 7.19 (d, 2H), 7.30 (d, 2H)

¹³C-NMR (125 MHz; CDCl₃): 15.6, 28.6, 35.4, 36.8, 37.8, 66.0, 69.0, 70.9, 78.6, 114.9, 119.1, 129.4, 129.7, 130.6, 133.1, 137.1, 157.9

Example 4a

3-[4-(2-{4-tert-Butoxycarbonylaminophenyl}ethoxy)phenyl]-(2S)-ethoxypropyl methanesulfonate The compound was synthesised in an analogous method as used in Example 4 using Example 3b (1.27 g, 99% yield).

¹H-NMR (400 MHz; CDCl₃): 1.17 (t, 3H), 1.53 (s, 9H), 2.68–2.78 (m, 2H), 3.02–3.07 (m, 5H), 3.47–3.63 (m, 2H), 3.65–3.72 (m, 1H), 4.05–4.28 (m, 5H), 6.46 (—NH), 6.83 (d, 2H), 7.12 (d, 2H), 7.21 (d, 2H), 7.31 (d, 2H)

Example 5

S-{3-[4-({4-tert-Butoxycarbonylaminophenyl}ethoxy)phenyl]-2-ethoxypropyl ethanethioate Example 4 (0.7 g, 1.4 mmole) was dissolved in DMF (3 ml) and caesium ethanethioate (1.0 g, 2.5 mmole) was added. After stirring at room temperature 48 hours it was checked using HPLC that the starting material was consumed. Water was added and the mixture was extracted three times with ethyl acetate. The organic phase was dried with magnesium sulfate and evaporated giving 0.57 g (84% yield) of the desired product.

¹H-NMR (500 MHz; CDCl₃): 1.10 (t, 3H), 1.50 (s, 9H), 2.33 (s, 3H), 2.70–2.76 (m, 2H), 2.92–3.08 (m, 4H), 3.35–3.41 (m, 1H), 3.49–3.55 (m, 2H), 4.09 (t, 2H), 6.60 (—NH), 6.80 (d, 2H), 7.09 (d, 2H), 7.18 (d, 2H), 7.29 (d, 2H)

¹³C-NMR (125 MHz; CDCl₃): 15.6, 28.6, 30.5, 30.8, 33.1, 35.4, 39.7, 65.7, 69.0, 79.6, 114.6, 114.8, 119.0, 129.7, 130.4, 130.6, 130.7, 133.1, 137.0, 153.1, 157.6

Example 6 tert-Butyl N-(4-2-[4(2-ethoxy-3-mercaptopropyl) phenoxy]ethylphenyl)carbamate Example 5 (0.32 g, 0.66 mmole) was dissolved in methanol (10 ml) and cooled to 0° C. and anhydrous potassium carbonate (0.11 g, 0.86 mmole) was added. After stirring at room temperature for 1 hour it was checked using HPLC that all the starting material was consumed. Water was added, methanol evaporated and the residue extracted three times with ethyl acetate. The organic phase was dried with magnesium sulfate and evaporated.

Purification of the crude product with preparative HPLC (Kromasil C8, 7 μm, 50×250 mm) using acetonitrile (80%) in ammonium acetate buffer (pH 7) as mobil phase gave 0.16 g (52% yield) of the desired product.

$^1$H-NMR (500 MHz; CDCl$_3$): 1.15 (t, 3H), 1.54 (s, 9H), 2.73–2.88 (m, 4H), 3.01–3.08 (t, 2H), 3.40–3.72 (m, 1H), 4.12 (t, 2H), 6.56 (—NH), 6.83 (d, 2H), 7.13 (d, 2H), 7.21 (d, 2H), 7.33 (d, 2H)

$^{13}$C-NMR (125 MHz; CDCl$_3$): 15.7, 28.6, 35.4, 39.2, 43.7, 65.6, 69.0, 79.7, 80.7, 114.7, 119.1, 129.8, 130.6, 130.7, 133.2, 137.1, 153.1, 157.6

Example 7 tert-Butyl N-[4-(2-(4-[(2S)-2-ethoxy-3-(ethylthio) propyl]phenoxy)ethyl)phenyl]carbamate Example 4a (0.32 g, 0.62 mmole) was dissolved in methanol (5 ml) and sodiumthioethoxide (0.21 g, 2.49 miole) was added. After stirring at room temperature for 26 hours it was checked using HPLC that all the starting material was consumed. Water was added, the methanol was evaporated and the residue extracted three times with ethyl acetate. The organic phase was dried with magnesium sulfate and evaporated. Purification of the crude product with preparative HPLC (Kromasil C8, 7 μm, 50×250 m=) using acetonitrile (70–100%) in ammonium acetate buffer (pH 7) as mobil phase gave 0.17 g (57% yield) of the desired product.

$^1$H-NMR (500 MHz; CDCl$_3$): 1.18 (t, 3H), 1.27 (t, 3H), 1.56 (s, 9H), 2.57–2.68 (m, 4H), 2.79–2.91 (m, 2H), 3.07 (t, 2H), 3.42–3.50 (m, 2H), 3.54–3.62 (m, 2H), 4.15 (t, 2H), 6.53 (—NH), 6.85 (d, 2H), 7.16 (d, 2H), 7.24 (d, 2H), 7.34 (d, 2H)

$^{13}$C—NMR (125 MHz;CDCl$_3$): 15.2, 15.8, 27.2, 28.7, 35.5, 35.8, 39.5, 65.6, 69.1, 81.1, 114.7, 119.1, 129.8, 130.7, 131.0, 133.2, 137.1, 157.6

Example 8

2-Ethoxy-3-[4-(2-{4-methylsulfonyloxyphenyl}ethoxy)phenyl-1-hydroxypropane

Ethyl 2-ethoxy-3-[4-(2-{4-(methylsulfonyloxyphenyl) ethoxy)phenyl]propanoate (1.1 g; 2.5 mmole) was dissolved in dichloromethane (10 ml) and cooled to −78° C. DIBAL-H (1M; 5.8 ml; 5.8 mmole) was added dropwise. The reaction mixture was stirred at −78° C. for 0.5 hours after which it was allowed to reach room temperature, after 2 hours it was checked using HPLC that all the starting material was consumed. The reaction mixture was cooled to −40° C. and quenched with sulfuric acid (2%, 5 ml). Hydrochloric acid (2M, 10 ml) was added and the mixture was extracted three times with ethyl acetate.

The organic phase was washed with sodium hydrogencarbonate, dried with magnesium sulfate and evaporated, giving 0.97 g (98% yield) of the desired product.

$^1$H-NMR (500 MHz; CDCl$_3$): 1.17 (t, 3H), 2.10 (OH), 2.64–2.71 (m, 1H), 2.77–2.84 (m, 1H), 3.08 (t, 2H), 3.11 (s, 3H), 3.38–3.63 (m, 5H), 4.14 (t, 2H), 6.80 (d,2H), 7.10 (d, 2H), 7.22 (d, 2H), 7.33 (d, 2H)

$^{13}$C-NMR (125 MHz; CDCl$_3$): 15.5, 35.1,36.4, 37.2, 63.6, 65.1, 68.1, 81.0, 114.4, 121.9, 130.3, 130.4, 130.5, 137.9, 147.8, 157.1

Starting Material (a) 2-(4-Methylsulfonyloxyphenyl)ethylmethanesulfonate

4-Hydroxyphenethylalcohol (15 g; 0.108 mole) was dissolved in dichloromethane. Triethylamine (27.3 g; 0.27 mole) was added followed by addition of a solution of methanesulfonyl chloride (27.2 g; 0.239 mole) in dichloromethane at 0° C. The reaction mixture was allowed to reach room temperature, then stirred at room temperature and followed by TLC. The reaction mixture was filtered. The filtrate was washed with water, the phases were separated and the organic phase was dried with sodium sulfate and evaporated in vacuo to give 28 g (yield 88%) of the desired product.

$^1$H-NMR (400 MHz;CDCl$_3$): 2.85 (s, 3H), 3.05 (t, 2H), 3.15 (s, 3H), 4.35 (s, 2H), 7.2 (dm, 2H), 7.25 (dm, 2H).

$^{13}$C-NMR (100 MHz; CDCl$_3$): 34.8,37.3, 69.6, 122.2, 130.5,135.8, 148.1.

(b) 4-[2-(4-Formylphenoxy)ethyl]phenylmethanesulfonate

Compound (a) (30 g; 0.102 mole) was dissolved in acetonitrile and slowly added to a mixture of 4-hydroxybenzaldehyde (31.1 g; 0.255 mole) and potassium carbonate (41.46 g; 0.3 mole) in acetonitrile and refluxed until (a) was consumed. The salts were filtered off, the solvent was evaporated in vacuo, and dichloromethane was added. The organic phase was washed with water and evaporated. Purification by chromatography on silica gel using dichloromethane as eluant gave 21.6 g (yield 66%) of the desired product.

$^1$H-NMR (400 MHz; CDC1,): 3.05–3.15 (t, 2H; s, 3H), 4.2 (t, 2H), 6.95 (dm, 2H), 7.2 (dm, 2H), 7.3 (dm, 2H), 7.8 (dm, 2H), 9.8 (s, 1H).

$^{13}$C-NMR (100 MHz; CDCl$_3$): 37.3, 38.3, 63.4, 116.1, 122.1, 129.2, 130.6, 132.6, 138.1, 147.7, 162.6, 191.7.

(c) 2-Ethoxy-3-{4-[2-(4-methanesulfonyloxyphenyl) ethoxy]phenyl}acrylic acid ethyl ester Tetramethylguanidine (1.73 g; 15.0 mmole) was slowly added to a solution of compound (b) (4.49 g; 14.0 mmole) and (1,2-diethoxy-2-oxoethyl)(triphenyl)phosphonium chloride (5.62 g; 13.1 mmole) in chloroform (50 ml) at 0° C. After stirring at room temperature overnight the solvent was evaporated in vacuo. When diethyl ether was added to the residue, triphenylphosphine oxide crystallized as white crystals which were filtered off. The filtrate was evaporated in vacuo. The residue was purified by chromatography on silica gel using ethyl acetate in heptane (gradient 1.25–100%) as eluants. The crude products crystallized upon standing. Recrystallization gave 2.18 g (yield 35%) of the desired product as white crystals.

$^1$H-NMR (500 MHz; CDCl$_3$): 1.34–1.38 (2t, 2×6H, J=7 Hz for both), 3.11 (t, 2H, J=6 Hz), 3.13 (s, 3H), 3.98 (q, 2H,J=7 Hz), 4.2 (t, 2H, J=6.8 Hz), 4.28 (q, 2H, J=7 Hz), 6.87 (dm, 2H, J=9 Hz, unresolved), 6.95 (s, 11H), 7.23 (dm, 2H, J=9 Hz, unresolved), 7.33 (dm, 2H, J=9 Hz, unresolved), 7,73 (dm, 2H, J=9 Hz, unresolved).

$^{13}$C-NMR (125 MHz; CDCl$_3$): 14.3, 15.5, 35.0, 37.3, 61.0, 67.5, 68.1, 114.4, 122.0, 123.8, 126.6, 130.5, 131.7, 137.7, 143.1, 147.9, 159.0, 164.9.

(d) Ethyl 2-ethoxy-3-[4-(2-{4-methylsulfonyloxyphenyl}ethoxy)phenyl]propanoate

Compound (c) (1.47 g; 3.38 mmole) was hydrogenated for 3 hours at atmospheric pressure in ethyl acetate (50 ml)

using Pd/C (0.74 g, 5%) as a catalyst. The reaction mixture was filtered through celite, dried (magnesium sulfate) and the solvent was evaporated in vacuo to give 1.44 g (yield 98%) of the desired product.

$^1$H-NMR (500 MHz; CDCl$_3$): 1.16 (t, 3H, J=7 Hz), 1.23 (t, 3H, J=7 Hz), 2.92–2.96 (in, 2H), 3.09 (t, 2H, J=6.6 Hz), 3.13 (s, 3H), 3.31–3.38 (in, 1H), 3.56–3.63 (in, 1H), 3.94–3.98 (in, 1H), 4.12–4.19 (in, 4H), 6.8 (dm, 2H, J=8.8 Hz, unresolved), 7.14 (dm, 2H, J=8.9 Hz, unresolved), 7.22 (dm, 2H, J=8.9 Hz, unresolved), 7.33 (dm, 2H, J=8.6 Hz, unresolved).

$^{13}$C-NMR (125 MHz; CDCl$_3$): 14.2, 15.0,35.1, 37.2, 38.4, 60.7, 66.1, 68.1, 80.3, 114.3, 121.9, 129.5, 130.4, 130.5, 138.0, 147.8, 157.4, 172.5.

Example 9

2-Ethoxy-3-[4-(2-{4-methylsulfonyloxyphenyl}ethoxy)phenyl-1-methoxypropane

Example 8 (0.45 g; 1.2 mmole) was dissolved in acetone (10 ml) and methyliodide (1.78 g; 12.5 mmole) and silver oxide (2.64 g, 11.4 mmole) was added. The reaction mixture was stirred at room temperature.

After 48 hours it was checked using HPLC that all the starting material was consumed. The reaction mixture was filtered through celite, acetone evaporated and the crude product was purified with preparative HPLC (Kromasil C8, 7 μm, 50×250 mm) using acetonitrile (65%) in ammonium acetate buffer (pH 7) as mobil phase gave 0.39 g (84% yield) of the desired product.

$^1$H-NMR (500 MHz; CDCl$_3$): 1.14 (t, 3H), 2.75 (d, 2H), 3.10 (t, 2H), 3.13 (s, 3H), 3.30–3.49 (m, 2H), 3.35 (s, 3H), 3.50–3.60 (s, 2H), 4.15 (t, 2H), 6.80 (d,2H), 7.12 (d, 2H), 7.22 (d, 2H), 7.33 (d, 2H)

$^{13}$C-NMR (125 MHz; CDCl$_3$): 15.5, 37.0, 37.3, 59.1, 65.3, 68.2, 73.9, 79.7, 114.3, 121.9, 130.4, 130.5, 131.1, 138.0, 147.8, 157.0

Example 10

2-Cyano-3-{4-[2-(4-methylsulfonyloxyphenyl)ethoxy]phenyl}propanol

Sodium borohydride (1.37 g, 36 mmol) was added in portions into a solution of ethyl 2-cyano-3-{4-[2-(4-methylsulfonyloxyphenyl)ethyl]phenyl}propanoate (3.0 g, 7.2 mmol) in methanol (40 ml). After addition, the mixture was stirred for 2 hours. Hydrochloric acid (10%) was then added dropwise into the mixture to a pH=4–5. The reaction mixture was evaporated in vacuum to remove methanol. The residue was extracted with ethyl acetate. The ethyl acetate solution was washed with brine and dried with magnesium sulfate. The solvent was removed in vacuum. Column chromatography of the residue on silica gel using ethyl acetate/heptane (20:80 till 60:40) as eluant gave 1.9 g (yield 70%) of the desired product.

$^1$H-NMR(300 MHz, CDCl$_3$): 2.27 (t, J=6 Hz, OH), 2.91(s, br, 3H), 3.10(t, J=7 Hz, 2H), 3.14(s, 3H), 3.70–3.80 (m, 2H), 4.16(t, =7 Hz, 2H), 6.85(d, J=9 Hz, 2H), 7.16(d, J=9 Hz, 2H), 7.23 (d, J=9 Hz, 2H) and 7.34(d, J=9 Hz, 2H).

$^{13}$C-NMR(75 MHz, CDCl$_3$): 33.63, 35.10, 36.99, 37.29, 61.76, 68.23, 114.83 (2C), 120.50, 122.0 (2C), 128.68, 130.15 (2C), 130.58 (2C), 137.92, 147.84 and 157.90.

Starting Material
(a) 2-Cyano-3-{4-[2-(4-methylsulfonyloxyphenyl)ethoxy] phenyl}acrylic acid ethyl ester A mixture of 4-[2-(4-formylphenoxy)ethyl]phenylmethanesulfonate (2 g; 6.24 mmole), ethyl cyanoacetate (1.41 g; 12.48 mmole) and sodium acetate (1.34 g; 15.6 mmole) was heated to 120° C. The mixture which melted upon heating was then allowed to cool down. Dichloromethane was added, the solution was washed with water and brine. The organic phase was dried with sodium sulfate, filtered and the solvent evaporated in vacuo. Chromatography of the crude product on silica gel using heptane:ethyl acetate (gradient 9:1 to 1:1) as eluant followed by crystallization gave 1.98 g (yield 77%) of the desired product.

$^1$H-NMR (400 MHz; CDCl$_3$): 1.37 (t, 3H, J=7.1 Hz), 3.13 (t, 2H, J=6.8 Hz), 3.13 (s, 3H),4.24 (t, 2H, J=6.8 Hz), 4.35 (q, 2H, J=7.1 Hz), 6.95 (dm, 2H, J=9 Hz, unresolved), 7.23 (dm, 2H, J=9 Hz, unresolved), 7.32 (dm, 2H, J=9 Hz, unresolved), 7.97 (dm, 2H, J=9 Hz, unresolved), 8.15 (s, 11H).

$^{13}$C-NMR (100 MHz; CDCl$_3$): 14.2, 34.9, 37.4, 62.4, 68.6, 99.6, 115.2, 116.1, 122.1, 124.6, 130.5, 133.6, 137.3, 148.0, 154.3, 162.8, 163.1.

(b) Ethyl 2-cyano-3-{4-[2 (4-methylsulfonyloxypbenyl) ethoxy]phenyl } propanoate A mixture of compound (a) (1.69 g; 4.07 mmole) and diethyl-1,4-dihydro-2,6-dimethyl-3,5-pyridine dicarboxylate (2.06 g; 8.14 mmole) was slowly heated to more than 190° C. under vacuum and thereafter allowed to cool to room temperature. The crude product was purified by chromatography on silica gel using heptane:ethyl acetate (gradient 2:1 to 1:1) as eluant to give 1.55 g (yield 91%) of the desired product.

$^1$H-NMR (400 MHz; CDCl$_3$): 1.17 (t, 3H, J=7 Hz), 2.96–3.16 (m, 6H), 3.66–3.72 (m, 1H), 4.05 (t, 2H, J=6.8 Hz), 4.13 (q, 2H, J=7 Hz), 6.73 (dm, 2H, J=8.5 Hz, unresolved), 7.09–7.19 (m, 4H), 7.25 (dm, 2H, J=8.5 Hz, unresolved).

$^{13}$C-NMR (100 MHz; CDCl$_3$): 13.4, 34.3, 34.5, 36.7, 39.3, 114.3, 116.0, 121.5, 127.2, 129.6, 130.1, 137.4, 147.5, 157.7, 165.2.

Example 11

2-Ethoxy-3-}4-[2-(4-ethyloxyphenyl)ethoxy]phenyl}propanol

In an analagous method to the preparation of Example 1 using ethyl 2-ethoxy-3-{4-[2-(4-ethyloxyphenyl)ethoxy]phenyl}propanoate (0.925 g, 2.393 mmol) and sodium borohydride (0.157 g, 4.14 mmol), the reaction was quenched after 24 hours, to give 0.723 g (yield 89%) of the desired product.

$^1$H-NMR (500 MHz; CDCl$_3$): 1.21 (t, 3H, J=7 Hz), 1.44 (t, 3H, J=7 Hz), 2.36 (bs, 1 OH), 2.69–2.75 (m, 1H), 2.81–2.87 (m, 1H), 3.06 (t, 2H, J=7.2 Hz), 3.45–3.51 (m, 1H), 3.51–3.60 (m, 3H), 3.60–3.67 (m, 1H), 4.04 (q, 2H, J=7 Hz), 4.14(t, 2H, J=7.2 Hz), 6.86 (dm, 2H, J=8.6 Hz, unresolved), 6.89 (dm, 2H, J=8.6 Hz, unresolved), 7.14 (dm, 2H, J=8.6 Hz, unresolved), 7.22 (dm, 2H, J=8.6 Hz, unresolved).

$^{13}$C-NMR (125 MHz; CDCl$_3$): 14.7, 15.4, 34.8, 36.4, 63.3, 63.5, 65.1, 68.8, 81.1, 114.36, 114.44, 129.8, 130.0, 130.0, 130.1, 157.2, 157.5.

Starting Material
(a) Ethyl 2-ethoxy-3-{4-[2-(4-ethyloxyphenylethoxy] phenyl}propanoate The compound was synthesised in an analogous method to the preparation in Example 3(d) using 2-[4 ethoxyphenyl]

ethanol (3.431 g, 20.64 mmol) and ethyl 2-ethoxy-3-(4-hydroxyphenyl)propanoate (4.919 g, 20.64 mmol). Purification by chromatography on silica gel using heptane:ethyl acetate (gradient 1:1 to 3:5) as eluants gave 6.3 g (yield 79%) of the desired product.

$^1$H-NMR (500 MHz; CDCl$_3$): 1.2 (t, 3H, J=7 Hz), 1.25 (t, 3H, J=7.1 Hz), 1.43 (t, 3H, J=7 Hz), 2.97–3.01 (m, 2H), 3.04 (t, 2H, J=7.1 Hz), 3.35–3.42 (m, 1H), 3.60–3.68 (m, 1H), 3.99–4.05 (m, 3H), 4.13(t, 2H, J=7.1 Hz), 4.19 (q, 2H, J=7.1 Hz), 6.85 (dm, 2H, J=8.6 Hz, unresolved), 6.87 (dm, 2H, J=8.6 Hz, unresolved), 7.18 (dm, 2H, J=8.6 Hz, unresolved), 7.20 (dm, 2H, J=8.6 Hz, unresolved).

$^{13}$C-NMR (125 MHz; CDCl$_3$): 14.0, 14.6, 14.9, 34.7, 38.3, 60.5, 63.1, 65.9, 68.7, 90.2, 114.1, 114.3, 129.0, 129.7, 129.9, 130.1, 157.4, 172.2.

Example 12

1-Cyano-2-[4-(2-{4-tert-butyloxycarbonylaminophenyl}ethoxy)phenyl]-1-ethoxyethane 1-Carbamoyl-2-[4-(2-{4-tert-butyloxycarbonylaminophenyl}ethoxy)phenyl]-1-ethoxyethane(0.63 g, 1.47 mmole) was dissolved in dioxane (20 ml) and pyridine (0.35 g, 4.41 mmole) was added. The mixture was placed in a ultrasonic bath for 5 minutes, then trifluoroacetic acid anhydride (0.37 g, 1.76 mmole) was added. After stirring at room temperature for 16 hours it was checked using HPLC that all the starting material was consumed. Sodium carbonate solution was added and extracted three times with dichloromethane. The organic phase was dried with magnesium sulfate and evaporated. Purification of the crude product with preparative HPLC (Kromasil C8, 7 μm, 50×250 mm) using acetronitrile (70–80%) in ammonium acetate buffer (pH 7) as mobil phase gave 0.47 g (75% yield) of the desired product.

$^1$H-NMR (400 MHz; CDCl$_3$): 1.25 (t, 3H), 1.54 (s, 9H), 3.00–3.12 (m, 4H), 3.46–3.55 (m, 1H), 3.78–3.87 (m, 1H), 4.13 (t, 2H), 4.22 (t, 2H), 6.53 (—NH), 6.86 (d, 2H), 7.17–7.24 (m, 4H), 7.31 (d, 2H)

$^{13}$C-NMR (100 MHz; CDCl$_3$): 15.0, 28.6, 35.3, 39.4, 66.6, 69.0, 70.6, 80.7, 114.9, 118.5, 119.1, 127.0, 129.8, 130.9, 133.1, 137.1, 153.1, 158.5

Starting Material (a) 1-Carbamoyl-2-[4-(2-{4-tert-butyloxycarbonylaminophenyl}ethoxy)phenyl]-1-ethoxyethane 3-{4-[2-(4-tert-Butoxycarbonylamino phenyl}ethoxy]phenyl]-2-ethoxypropanoic acid (1.18 g, 2.75 mmole) and benzotriazol-1-yl-oxytri-pyrrolidinophosphoniumhexafluorophosphate (1.43 g, 2.75 mmole) were dissolved in dry DMF (20 ml). Ammonia gas was bubbled through the mixture for 5 minutes. After stirring at room temperature for 16 hours it was checked using HPLC that all the starting material was consumed. Water was added and extracted three times with ethyl acetate dried with magnesium sulfate and evaporated. The residue was redissolved in dichloromethane and chromatography on silica using a gradient system of dichloromethane:methanol (0–5%) gave 1.04 g (85% yield) of the desired product.

$^1$H-NMR (500 MHz; CDCl$_3$): 1.16 (t, 3H), 1.55 (s, 9H), 2.85–2.92 (m,1H), 3.06 (t, 2H), 3.08–3.14 (m, 1H), 3.41–3.48 (m, 1H), 3.50–3.58 (m, 1H), 3.92 (q, 1H), 4.14 (t, 2H), 5.91 (—NH2), 6.62 (—NH2), 6.72 (—NH,), 6.84 (d, 2H), 7.18 (d, 2H), 7.34 (d, 2H)

$^{13}$C-NMR (125 MHz; CDCl$_3$): 15.5, 28.6, 35.4, 38.4, 66.9, 69.0, 81.7, 114.5, 119.1, 129.8, 130.9, 133.2, 137.1, 157.8, 175.8

(b) 3-{4-[2-(4-tert-Butoxycarbonylaminophenyl)ethoxy]phenyl}-2-ethoxypropanoic acid Lithium hydroxide hydrate (77 mg; 1.85 mmole) in water (5.5 ml) was slowly added to a solution of ethyl 3-{4-[2-(4-tert-butoxycarbonylaminophenyl)ethoxy]phenyl}-2-ethoxypropanoate (0.77 g; 1.68 mmole) in THF (7.6 ml). After stirring at room temperature for 4 hours the reaction mixture was kept in a freezer for 4 days. THF was removed by evaporation in vacuo. More water was added and the mixture was acidified with hydrochloric acid to pH1. The product was extracted with ethyl acetate, washed twice with water, dried (sodium sulfate), filtered and the solvent was evaporated in vacuo to give 0.712 g (98.7% yield) of the desired product.

$^1$H-NMR (400 MHz; CDCl$_3$): 1.18 (t, 3H, J=7 Hz), 1.54 (s, 9H), 2.93–3.10 (m, 4H), 3.36–3.45 (m, 1H), 3.60–3.69 (m, 1H), 4.02–4.07 (m,1H), 4.12 (t, 2H, J=7 Hz), 6.83 (dm, 2H, J=8.8 Hz, unresolved), 7.15–7.23 (m, 4H), 7.27–7.34 (m, 2H), 10.28 (bs, 1NH).

$^3$C-NMR (100 MHz; CDCl$_3$): 15.0, 28.3, 35.2, 38.0, 66.7, 68.8, 79.9, 80.7, 114.6, 119.1, 129.0, 129.4, 130.4, 133.1, 136.8, 153.2, 157.8, 175.3.

Example 13 tert-Butyl 4-(2-{4-[(2S)-3-amino-2-ethoxypropyl]phenoxy}ethyl)phenylcarbamate (2S)-3-[4-(2-{4-[(tert-Butoxycarbonyl)amino]phenyl}ethoxy)phenyl]-2-ethoxypropyl methanesulfonate (described in Example 4a) (0.43 g, 0.87 mmole) was dissoved in dry DMF (5 ml). Sodium azide (0.23 g, 3.50 mmole) was added and the reaction mixture was heated to 80° C. and stirred overnight. The reaction was quenched with water and extracted with diethyl ether. The organic phase was washed with water, dried with magnesium sulfate and evaporated. The crude product was dissolved in dry diethyl ether and added to a solution of LAH (0.10 g, 2.62 mmole) in dry diethyl ether (50 ml). After one hour the reaction was quenched with water (0.5 ml), 5 M NaOH (1 ml) and water (0.5 ml) again. The mixture was refluxed for half an hour and the white precipitate was filtered off and the filtrate dried with magnesium sulfate and evaporated giving 0.63 g (72% yield) of the product.

$^1$H-NMR (500 MHz; CDCl$_3$): 1.19 (t, 3H), 1.35 (—NH2), 1.53 (s, 9H), 2.60–2.68 (m, 2H), 2.72–2.85 (m, 2H), 3.04 (t, 2H), 3.37–3.44 (m, 1H), 3.45–3.59 (m, 2H), 4.12 (t, 2H), 6.79 (—NH), 6.82 (d, 2H), 7.10 (d, 2H), 7.20 (d, 2H), 7.32 (d, 2H)

$^{13}$C-NMR (125 MHz; CDCl$_3$): 15.9, 28.6, 35.4, 38.0, 45.2, 65.4, 69.1, 80.6, 82.9, 114.8, 119.0, 129.8, 130.5, 131.0, 133.1, 137.2, 153.2, 157.5

Example 14

N-(4-{2-[4-(2-Cyano-3-hydroxypropyl)phenoxy]ethyl}phenyl)-2-methylpropanamide

Ethyl 2-cyano-3-(4-{2-[4-(isobutyrylamino)phenyl]ethoxy}phenyl)propanoate (0.5 g, 1.22 mmol) was dissolved in methanol (10 ml). Sodium borohydride (0.24 g, 6.34 mmol) was added carefully. The mixture was stirred at room temperature for 4 hours and then evaporated in vacuum to dry. Ethyl acetate and water were added into the residue. After separation, the organic phase was washed with 0.3 M hydrochloric acid, water and brine. The solvent was evaporated in vacuum. Column chromatography of the residue on silica gel using ethyl acetate/heptane as eluant gave 0.33 g desired product, yield 74%.

¹H-NMR (400 MHz, CDCl₃): 1.24 (6H, d), 2.51 (1H, m), 2.61 (1H, bdd), 2.90 (3H, m), 3.04 (2H, t), 3.73 (2H, m), 4.12 (2H, t), 6.83 (2H, d), 7.13 (2H, d), 7.22 (2H), 7.38 (1H, bs), 7.46 (2H, d)

¹³C-NMR (100 MHz, CDCl₃): 20.67, 34.75, 36.30, 37.67, 38.02, 62.81, 69.78, 115.97, 121.27, 121.62, 129.62, 130.57, 131.16, 135.28, 137.51, 159.12, 176.60

Starting Material (a) N-[4-(2-Hydroxyethyl)phenyl]-2-methylpropanamide

4-Aminophenylethyl alcohol (21 g, 0.153 mol) was dissolved in acetone (200 ml). The solution was heated to reflux and 2-methylpropionic anhydride (24.15 g, 0.153 mol) was added dropwise. The mixture was heated to reflux for 1 hour and HPLC showed the reaction was not complete. More (1.0 g) of 2-methylpropionic anhydride was added and it was refluxed for 1.5 hours more. The reaction mixture was then evaporated in vacuum to dry. The residue was dissolved in warm dichloromethane (150 ml) and then cooled down to room temperature. Heptane (200 ml) was dropped into the solution and crystals fell out. The crystals were filtered and washed with heptane. 30.7 g of titled product was obtained, yield 97%.

¹H-NMR (500 MHz, CDCl₃): 1.20 (6H, d), 2.59 (1H, m), 2.80 (2H, t), 3.40 (1H, t), 3.78 (2H, dt), 7.14 (2H, d), 7.54 (2H, d), 8.77 (1H, bs)

(b) Ethyl 2-cyano-3-(4-{2-[4-(isobutyrylamino)phenyl]ethoxy} phenyl)propanoate

Ethyl 2-cyano-3-(4-hydroxyphenyl)propanoate (1 g, 4.56 mmol) and N-[4-(2-hydroxyethyl)phenyl]-2-methylpropanamide (1.42 g, 6.85 mmol) were mixed in dichloromethane (40 ml). 1,1'-(Azodicarbonyl)dipiperidine (2.3 g, 9.12 mmol) and triphenylphosphine (2.4 g, 9.15 mmol) were then added respectively. The mixture was stirred overnight and filtered. The filtrate was evaporated to dry in vacuum. Column chromatography of the residue on silica gel using ethyl acetate/heptane as eluant gave 0.5 g desired product, yield 27%.

¹H-NMR (400 MHz, CDCl₃): 1.2–1.3 (9H, m), 2.49 (1H, m), 3.04 (2H, t), 3.08–3.23 (2H, 2dd), 3.66 (1H, dd), 4.11 (3H, m), 4.22 (2H, q)

Example 15

2-{4-[2-(4-Ethylphenyl)ethoxy]benzyl}-3-hydroxypropanenitrile

Methyl 2-cyano-3-{4-[2-(4-ethylphenyl)ethoxy]phenyl}propanoate (0.31 g, 0.9 mmole) was dissolved in methanol. Sodium borohydride (0.17 g, 4.5 mmole) was added and the rection mixture was stirred until TLC showed that all the starting material was consumed. HCL (1M) was added until pH ~4–5. The methanol was evaporated and the residue extracted with ethyl acetate. Further work-up and purification gave 0.15 g, 54%, of 2-{4-[2-(4-ethylphenyl)ethoxy]benzyl}-3-hydroxypropanenitrile.

¹H-NMR (400 MHz, MeOD): 1.18 (3H,t), 2.58 (2H, q), 2.74–2.91 (3H, m), 2,98 (2H, t), 3.58–3.70 (2H, m), 4.10 (2H, t), 6.84 (2H, d), 7.08–7.18 (6H, d+m)

¹³C-NMR (100 MHz, MeOD): 15.9, 29.2, 34.4, 36.0, 38.0, 62.0, 69.7, 115.4, 121.6, 128.6, 129.7, 130.2, 130.9, 136.6, 143.2, 159.1

Starting Material (a) Methyl 2-cyano-3-{4-[2-(4-ethylphenyl)ethoxy]phenyl}propanoate 2-(4-Ethylphenyl)ethanol (0.8 g, 5.3 mmole) and methyl 2-cyano-3-(4-hydroxyphenyl)propanoate (0.9 g, 4.4 mmole) was dissolved in dry dichloromethane.(20 ml). Triphenylphosphine (2.3 g, 8.8 mmole) was added followed by addition of ADDP (2.22 g, 8.8 mmole) resulting in a dark orange solution. The reaction mixture was stirred over night and then filtrated and evaporated. The residue was treated with a mixture of dichloromethane and diethyl ether and filtrated once again. SiO₂ was added to the filtrate which then was evaporated. Chromatography of the residue with diethyl ether/pentane (1:1) yielded 00.31 g, 20.8%, of methyl 2-cyano-3-{4-[2-(4-ethylphenyl)ethoxy]phenyl}propanoate.

¹H (300 MHz, CDCl₃): 1.25 (3H, t), 2.65 (2H, q), 3.10 (2H, t), 3.20 (2H, m), 3.70 (1H, m), 3.80 (3H, s), 4.15 (2H, t), 6.90 (2H, d), 7.10–7.25 (6H, m)

¹³C (75 MHz, CDCl₃): 15.7, 28.5, 35.0, 35.4, 39.8, 53.5, 68.8, 114.9, 116.2, 127.2, 128.0, 129.0, 130.2, 135.3, 142.5, 158.5, 166.1

Example 16

3-(4-{2-[4-(Methylsulfonyl)phenyl]ethoxy}phenyl)-2-(phenylthio)propan-1-ol

Ethyl 3-(4-{2-[4-(methylsulfonyl)phenyl]ethoxy}phenyl)-2-(phenylthio)propanoate (0.58 g, 1.20 mmole) was dissolved in dry dichloromethane (15 ml). The solution was cooled to –78° C. and DIBAL-H (1M hexan solution, 3.0 ml, 3.0 mmole) was added. The cooling agent was removed after 20 min. After 2 h the reaction mixture was cooled on an ice-bath before the addition of HCl (1M, 15 ml). The mixture was extracted with dicloromethane, the organic phase was washed twice with water (15 ml) and dried with NaSO₄. Evaporation gave 0.554 g, ~100%; of the desired product as a colorless oil.

¹H (300 MHz, CDCl₃): 2.87 (2H, d), 3.03 (3H, s), 3.16 (2H, 7), 3.32–3.42 (1H, m), 3.46–3.63 (2H, m), 4.18 (2H, t), 6.80 (2H, d), 7.10 (2H, d), 7.25 (3H, m), 7.40 (2H, m), 7.50 (2H, d), 7.85 (2H, d)

The starting material is described in the priority application of WO9962871.

Example 17

2-(4-{2-[4-(Methylsulfonyl)phenyl]ethoxy}benzyl)butan1-ol

Methyl 2-(4-{2-[4-(methylsulfonyl)phenyl]ethoxy}benzyl)butanoate (0:40 g; 1.02 mmole) was dissolved in dry methylene chloride (10 ml) and cooled to –78° C. 1 M DIBAH (3.00 ml; 3.00 mmole) was slowly added and the reaction was stirred over night and allowed to reach r.t. The reaction was cooled to –10° C. and quenched with hydrochloric acid (2 M, 5 ml) and extracted with methylene chloride. The organic phase was dried with magnesium sulfate. Purification of the crude product with preparative HPLC (Kromasil C8, 7 μm, 50×250 nmm) using acetonitrile (50%) in ammonium acetate buffer (pH 7) as mobil phase gave 0.24 g (63% yield) of the desired product.

¹H-NMR (400 MHz; CDCl₃): δ 0.92 (t, 3H), 1.28–1.46 (m, 2H), 1.36 (—OH), 1.62–1.72 (m, 1H), 2.52–2.62 (m, 2H), 3.04 (s, 3H), 3.17 (t, 2H), 3.51 (d, 2H), 4.19 (t, 2H), 6.76–6.82 (m, 2H), 7.05–7.10 (m, 2H), 7.49 (d, 2H), 7.87 (d, 2H)

¹³C-NMR (100 MHz; CDCl₃): δ 11.3, 23.2, 35.7, 36.3, 44.2, 44.5, 64.4, 67.7, 114.4, 127.5, 130.0, 130.1, 133.3, 138.7, 145.3, 156.7

Starting Material (a) Methyl 2-(4-{2-[4-(methylsulfonyl)phenyl]ethoxy}benzyl)butanoate Methyl 2-(4-hydroxybenzyl)butanoate (0.50 g; 2.5 mmole) and 2-[4-(methylsulfonyl)phenyl]ethanol (0.52 g, 2.5 mmole) were mixed in dichloromethane (10 ml). ADDP (0.76 g, 3.0 mmole) was added followed by addition of triphenylphosphine ((0.79 g, 3.0 mmole). The reaction was interrupted after 16 hours. Triphenylphosphine oxide formed in the reaction was filtered off and the filtrate was evaporated. Chromatography of the crude material from methanol and dichloromethane, gradient elution from 0–32% gave 0.64 g (66% yield) of the product.

$^1$H-NMR (400 MHz; CDCl$_3$): δ 0.88 (t, 3H), 1.47–1.66 (m, 2H), 2.48–2.57 (m, 1H), 2.66 (dd, 1H), 2.84 (dd, 1H), 3.01 (s, 3H), 3.14 (t, 2H), 3.58 (s, 3H), 4.16 (t, 2H), 6.74–6.79 (m, 2H), 7.03 (d, 2H), 7.46 (d, 2H), 7.85 (d, 2H)

$^{13}$C-NMR (100 MHz; CDCl$_3$): δ 11.6, 24.9, 35.5, 37.1, 44.4, 49.4, 51.2, 67.5, 114.3, 127.4, 129.7, 129.9, 131.8, 138.6, 145.2, 156.9, 175.8

Example 18

2-(4-{2-[4-(Methoxymethyl)phenyl]ethoxy}benzyl)butan-1-ol

The compound was synthesised in an analogous method to Example 17 using methyl 2-(4-{2-[4-(methoxymethyl)phenyl]ethoxylbenzyl)butanoate (0.427 g, 1.20 mmole) and DIBAL (1M, 4.76 ml, 4.76 mmole) to give 0.383 g (yield 97%) of the desired product.

$^1$H-NMR (400 MHz; CDCl$_3$): 0.92 (t, 3H, J=7.5 Hz), 1.29–1.42 (m, 3H), 1.60–1.72 (m, 1H), 2.55 (d, 2H, J=7.0 Hz), 3.06 (t, 2H, J=7.1 Hz), 3.37 (s, 3H), 3.50 (t, 2H, 3=5.3 Hz), 4.13 (t, 2H, J=7.1 Hz), 4.43 (s, 2H), 6.79 (dm, 2H, J=8.8 Hz, unresolved), 7.07 (dm, 2H, J=8.8 Hz, unresolved), 7.25–7.28 (m, 4H).

$^{13}$C-NMR (100 MHz; CDCl$_3$): 11.3, 23.2, 35.5, 36.3, 44.2, 58.0, 64.4, 68.6, 74.4, 114.4, 127.9, 129.0, 130.0, 132.9, 136.3, 137.5, 157.0.

Starting Material (a) [4-(Methoxymethyl)phenyl]acetic acid 4-(Bromomethyl)phenylacetic acid (4.85 g, 21.17 mmole), sodium methoxide (30% in methanol, ~12 ml, ~65 mmole)) and methanol (30 ml) were mixed and refluxed over night. The reaction mixture was allowed to cool down and was then acidified with HCL (1M). Methanol was evaporated. Water was added and the reaction mixture was extracted three times with dichloromethane. The combined organic phases was washed with brine and dried with NA$_2$SO$_4$. Evaporation gave 3.6 g, 94.4%, of the desired product.

$^1$H-NMR (300 MHz, CDCl$_3$): 3.40 (3H, s), 3.65 (2H, s), 4.45 (2H, s), 7.25–7.35 (4H, m), 11.05 (OH, bs)

(b) 2-[4-(Methoxymethyl)phenyl]ethanol

[4-(Methoxymethyl)phenyl]acetic acid (3.6 g, 20 mmole) was dissolved in THF (100 ml) and cooled on an ice-bath. BH$_3$xTBT (1M, 40 ml, 40 mmole) was added. The reaction mixture was stirred for 6 h and then quenched with HCl (1M, 80 ml) and water (~100 ml). THF was evaporated and the residue extracted with diclomethane and ethyl acetate. The phases were separated and the organic phase was washed with HCl (0.3M, 100 ml and dried with Na$_2$SO$_4$. Evaporation gave 3.31 g, 99.6%, of the desired product.

$^1$H-NMR (300 MHz, CDCl$_3$): 2.85 (2H, t), 3.35 (3H, s), 3.85 (2H, m), 4.45 (2H, s), 7.20 (2H, d), 7.30 (2H, d)

(c) Methyl 2-(4-{2-[4-(methoxymethyl)phenyl]ethoxy}benzyl)butanoate

ADDP (1,23 g, 4,89 mmole) and triphenylphosphine (1,03 g, 3,92 mmole) were added to a solution of 2-[4-(methoxymethyl)phenyl]ethanol (0,54 g, 3,26 mmole) and methyl 2-(4-hydroxybenzyl)butanoate (0,68 g, 3,26 mmole) in dry dichloromethane (10 ml) under argon. After 5 minutes, more dichloromethane (10 ml) was added. The reaction mixture was stirred at room temperature for 5.5 hours and then filtered. Purification by chromatography on silica gel using heptan:ethyl acetate (1:1) as eluent gave a mixture of product and starting material wich was dissolved in ethyl acetate and washed 3 times with 1 N sodium hydroxide. The organic phase was washed with brine, dried (sodium sulphate), filtered and solvent was evaporated to give 0,27 g (yield 60%) of the desired product.

$^1$H-NMR (400 MHz; CDCl$_3$): 0.95 (t, 3H, J=7.5 Hz), 1.55–1.65 (m, 1H), 1.65–1.75 (m, 1H), 2.56–2.64 (m, 1H), 2.70–2.76 (m, 1H), 2.89–2.95 (m, 1H), 3.11 (t, 2H, J=7.1 Hz), 3.42 (s, 3H), 3.64 (s, 3H), 4.17 (t, 2H, J=7.1 Hz), 4.48 (s, 2H), 6.84 (dm, 2H, J=8.6 Hz, unresolved), 7.09 (dm, 2H, J=8.3 Hz, unresolved), 7.28–7.35 (m, 4H).

$^{13}$C-NMR (100 MHz; CDCl$_3$): 11.6, 24.9, 35.4, 37.2, 49.3, 51.2, 57.9, 68.4, 74.3, 114.3, 127.8, 128.9, 129.6, 131.4, 136.2, 137.6, 157.1, 175.9.

Example 19

N-[2-Hydroxy-1-(4-{2-[4-(methoxymethyl)phenyl]ethoxyl}benzyl)ethyl]-2-methylpropanamide N-isobutyryl-O-{2-[4-(methoxymethyl)phenyl]ethyl}tyrosine (0.4 g, 1 mmol) was dissolved in dichloromethane (3 ml, dry). Pyridine (85 ml, 1.05 mmol, dry) was added. The mixture was cooled to −20° C. Under nitrogen atmosphere, cyanuric fluoride (200 ml, 2.2 mmol) was added. After the mixture was stirred at −20° C. to −7° C. for 1 hour, ice-cold water (10 ml) and dichloromathane (10 ml) were added. The phases were separated. The water phase was extracted with dichloromethane. The organic phases were combined and washed with ice-cold water (10 ml) and dried with sodium sulfate and concentrated to ca. 3 ml. Sodium borohydride (76 mg, 2 mmol) was added and then methanol (2 ml) was added dropwise in 15 minutes. After 15 minutes additional stirring, the mixture was neutralized with potassium hydrogensulfate (2M, 2 ml) and water (15 ml). The dichloromethane was evaporated in vacuum. The residue was extracted with ethyl acetate (30 ml×2). The organic phases were combined and washed with potassium hydrogensulfate (1M, 20 ml), water and brine and dried with sodium sulfate. The solvent was evaporated in vacuum.

Column chromatography of the residue on silica gel using ethyl acetate/heptane/isopropyl alcohol (45:45:10) as eluant gave 0.22 g desired product, yield 57

$^1$H-NMR (400 MHz, CDCl$_3$): 1.10 (6H, 2d), 2.32 (1H, m), 2.81 (2H, 2dd), 3.09 (3H, t+bs), 3.40 (3H, s), 3.60 (1H, m), 3.66 (1H, m), 4.07–4.18 (3H, t+m), 4.45 (2H, s), 5.75 (1H, bs), 6.84 (2H, d), 7.12 (2H, d), 7.29 (4H, 2d)

$^{13}$C-NMR (100 MHz, CDCl$_3$): 19.50, 19.68, 35.54, 35.69, 36.08, 52.89, 58.12, 64.52, 68.72, 74.54, 114.77, 128.02, 129.06, 129.70, 130.20, 136.42, 137.74, 157.64, 177.82

Starting Material (a) Methyl N-isobutyryltyrosinate

Sodium carbonate (5.78 g, 0.054 mol) in water (50 ml) was added into tyrosinmethylester hydrochloride (25 g, 0.108 mol) in dichloromethane (500 ml). The mixture was stirred vigorously and cooled to 0° C. Isobutyryl chloride (12.3 ml, 0.119 mol) and sodium carbonate (8.58 g in 50 ml water, 0.081 mol) were dropped in from two adding funnels respectively. The resulting mixture was stirred for 2 hours at 0° C. and then at room temperature overnight. HPLC showed the reaction was not complete. More isobutyryl chloride (6.15 ml, 0.059 mol) and sodium carbonate (5.78 g in 50 ml water, 0.054 mol) were dropped in. The mixture was stirred for 6 hours more and then filtered. The crystals were washed with water and diethyl ether. White crystal product (27 g) was obtained, yield 94%.

$^1$H-NMR (400 MHz, CDCl$_3$): 0.98 (3H, d), 1.04 (3H, d), 2.43 (1H, m), 2.85 (1H, dd), 3.04 (1H, dd), 3.67 (3H, s), 4.57 (1H, dd), 4.84 (2H, s), 6.69 (2H, d), 7.00 (2H, d)

(b) Methyl N-iso-Butyryl-O-{2-[4-(methoxymethyl)phenyl]ethyl}tyrosinate

2-[4-(Methoxymethyl)phenyl]ethanol (0.6 g, 3.61 mmol) and methyl N-isobutyryltyrosinate (1.15 g, 4.34 mmol) were mixed in dichloromethane (20 ml, dry). 1,1'-(Azodicarbonyl)dipiperidine (1.1 g, 4.36 mmol) and triphenylphosphine (1.14 g, 4.35 mmol) were then added respectively. The mixture was stirred at room temperature overnight and filtered. The filtrate was evaporated in vacuum to dry. Column chromatography of the residue on silica gel using ethyl acetate/heptane (gradient 5:95 to 50:50) as eluant gave 0.71 g desired product, yield 48%.

$^1$H-NMR (400 MHz, CDCl$_3$): 1.14 (6H,d), 2.36 (1H, m), 3.02–3.17 (4H, m), 3.40 (3H, s), 3.75 (3H, s), 4.15 (2H, t), 4.46 (2H, s), 4.86 (1H, dd), 5.87 (1H, d), 6.82 (2H, d), 6.99 (2H, d), 7.31 (4H, m)

(c) N-isobutyryl-O-{2-[4-(methoxymethyl)phenyl]ethyl}tyrosine

Methyl N-isobutyryl-O-{2-[4-(methoxymethyl)phenyl]ethyl}tyrosinate (0.7 g, 1.69 mmol) was dissolved in dioxane (6 ml). Lithium hydroxide monohydrate (0.25 g, 5.95 mmol) in water (6 ml) was added. The mixture was stirred overnight and then diluted with water and evaporated in vacuum to remove dioxane. The residue was acidified with 1M hydrochloric acid, pH ~3 and then extracted twice with dichloromethane. The organic phase was washed with brine and dried with sodium sulfate. The solvent was then evaporated. 0.67 g desired product was obtained, yield 99%.

$^1$H-NMR (400 MHz, CDCl$_3$): 1.13 (6H, d), 2.38 (1H, m), 3.09 (3H, t+dd), 3.17 (1H, dd), 3.41 (3H, s), 4.15 (2H, m), 4.46 (2H, s), 4.82 (1H, m), 5.93–6.03 (1H, 2d), 6.80 (2H, d), 7.04 (2H, d), 7.29 (4H,2d)

Example 20

IV-(1-{4-[2-(4-Ethoxyphenylethoxy]benzyl}-2-hydroxyethyl)-2-methylpropanamide

O-[2-(4-ethoxyphenyl)ethyl]-N-isobutyryltyrosine (186 mg, 0.47 mmol) was dissolved in dichloromethane (1.5 ml, dry). Pyridine (40 ml, 0.5 mmol, dry) was added. The mixture was cooled to −20° C. Under inert gas, cyanuric fluoride (90 ml, 1 mmol) was added. After the mixture was stirred at −20° C. for 1 hour, ice-cold water (10 ml and dichloromethane (15 ml) were added. The phases were separated. The water phase was extracted with dichloromethane (15 ml). The organic phases were combined and washed with ice-cold water (10 ml) and dried with sodium sulfate and concentrated to ca. 2 ml. Sodium borohydride (38 mg, 1 mmol) was added and then methanol (1 ml) was added dropwise in 10 minutes. After 10 minutes additional stirring, the mixture was neutralized with 2M potassium hydrogensulfate and water. The dichloromethane was evaporated in vacuum. The residue was extracted with ethyl acetate (20 ml×2). The organic phases were combined and washed with potassium hydrogensulfate (1M, 15 ml), water and brine and dried with sodium sulfate. The solvent was evaporated in vacuum. Column chromatography of the residue on silica gel using ethyl acetate/heptane/isopropyl alcohol (45:45:10) as eluant gave 0.12 g desired product, yield 67

$^1$H-NMR (400 MHz, CDCl$_3$): 1.10 (6H, 2d), 1.42 (3H, t), 2.32 (1H, m), 2.82 (2H, 2dd), 3.23 (1H, bs), 3.60 (1H, m), 3.66 (1H, m), 4.03 (2H, q), 4.12 (3H, t+m), 5.79 (1H, bd), 6.85 (4H, 2d), 7.12 (2H, d), 7.19 (2H, d)

$^{13}$C-NMR (100 MHz, CDCl$_3$): 14.91, 19.50, 19.69, 34.95, 35.69, 36.09, 52.88, 63.48, 64.42, 69.03, 114.56, 114.76, 129.66, 129.94, 130.13, 130.20, 157.68, 177.83

Starting Material (a) Methyl O-[2-(4-ethoxyphenyl)ethyl]-N-isobutyryl tyrosinate 4-Ethoxy-phenethyl alcohol (0.6 g, 3.61 mmol) and methyl N-isobutyryltyrosinate (1.15 g, 4.34 mmol) were mixed in dichloromethane (20 ml, dry). 1,1'-(Azodicarbonyl)dipiperidine (1.1 g, 4.36 mmol) and triphenylphosphine (1.14 g, 4.35 mmol) were then added respectively. The mixture was stirred at room temperature overnight and filtered. The filtrate was evaporated in vacuum to dry. Column chromatography of the residue on silica gel using ethyl acetate/heptane (gradient 10:90 to 50:50) as eluant gave 0.75 g desired product, yield 50%.

$^1$H-NMR (400 MHz, CDCl$_3$): 1.14 (6H, d), 1.42 (3H,t), 3.01–3.16 (4H, m), 3.48 (3H, s), 4.04 (2H, q), 4.12 (2H, t), 4.86 (1H, dd), 5.85 (1H, bd), 6.80–6.90 (4H, 2d), 6.99 (2H, d), 7.20 (2H, d)

(b) O-[2-(4-Ethoxyphenyl)ethyl]-N-isobutyryltyrosine

Methyl O-[2-(4-ethoxyphenyl)ethyl]-N-isobutyryltyrosinate (0.25 g, 0.61 mmol) was dissolved in dioxane (4 ml). Lithium hydroxide monohydrate (0.1 g, 2.38 mmol) in water (4 ml) was added. The mixture was stirred overnight and then acidified with 1M hydrochloric acid, pH ~3–4. Dioxane was removed by evaporation in vacuum. The residue was diluted with water and then extracted with dichloromethane. The organic phase was washed with brine and dried with sodium sulfate. The solvent was then evaporated. 0.25 g desired product was obtained, yield 100%.

$^1$H-NMR (400 MHz, CDCl$_3$): 1.13 (6H, dd), 1.42 (3H,t), 2.36 (1H, m), 3.03 (2H, t), 3.09 (1H, dd), 3.20 (1H, dd), 4.05 (2H, q), 4.11 (2H, t), 4.82 (1H, dd), 5.89 (1H, d), 6.85 (4H, 2d), 7.07 (2H, d), 7.19 (2H, d)

Example 21

2-Ethoxy-3-{4-[2-(4-ethylphenyl)ethoxy]phenyl}propan-1-ol

2-Ethoxy-3-{4-[2-(4-ethylphenyl)ethoxy]phenyl}propanoic acid (0.48 g, 1.4 mmol) was dissolved in tetrahydrofiran (15 ml, dry) and it was then cooled in an ice-bath. Borane-tetrahydrofuiran complex (1M in tetrahydrofiran, 3 ml, 3 mmol) was added. After the addition, the ice-bath was removed. The reaction mixture was stirred 4 hours at room temperature and then quenched with 1M hydrochloric acid and water. Tetrahydrofuran was evaporated in vacuum.

The residue was diluted with water and then extracted with dichloromethane. The organic phase was washed with brine and dried with sodium sulfate. The solvent was then evaporated. The desired product (0.42 g) was obtained, yield 91%.

$^1$H-NMR (400 MHz, CDCl$_3$): 1.25 (3H, t), 1.31 (3H, t), 2.04 (1H, bs), 2.68–2.80 (3H, q+dd), 2.87 (1H, dd), 3.13

(2H, t), 3.50–3.72 (5H, m), 4.20 (2H, t), 6.91 (2H, d), 7.18 (2H, d), 7.23 (2H, d), 7.28 (2H, d)

$^{13}$C-NMR (125 MHz, CDCl$_3$): 15.42, 15.52, 28.35, 35.28, 36.38, 63.50, 65.10, 68.68, 81.15, 114.35, 127.83, 128.81, 130.15, 135.25, 142.22, 157.24

Starting Material (a) Ethyl 2-ethoxy-3-{4-[2-(4-ethylphenyl)ethoxy]phenyl}propanoate 4-Ethyl-phenyl alcohol (0.45 g, 3 mmol) and ethyl 2-ethoxy-3-(4-hydroxyphenyl)propanoate (0.86 g, 3.6 mmol) were mixed in dichloromethane (15 ml). 1,1'-(Azodicarbonyl)dipiperidine (0.91 g, 3.6 mmol) and triphenylphosphine (0.95 g, 3.6 mmol) were then added respectively. The mixture was stirred at room temperature overnight and filtered. The filtrate was evaporated to dry in vacuum. Column chromatography of the residue on silica gel using ethyl acetate/heptane (gradient 10:90 to 50:50) as eluant gave 0.49 g desired product, yield 44%.

$^1$H-NMR (500 MHz, CDCl$_3$): 1.17 (3H, t), 1.24 (6H, 2t), 2.64 (2H, q), 2.95 (2H, dd), 3.06 (2H, t), 3.35 (1H, dt), 3.60 (1H, dt), 3.96 (1H, dd), 4.15 (4H, m), 6.82 (2H, d), 7.15 (4H, 2d), 7.21 (2H, d)

(b) 2-Ethoxy-3-{4-[2-(4-ethylphenyl)ethoxy]phenyl}propanoic acid

Ethyl 2-ethoxy-3-{4-[2-(4-ethylphenyl)ethoxy]phenyl}propanoate (0.48 g, 1.3 mmol) was dissolved in dioxane (5 ml). Lithium hydroxide monohydrate (0.2 g, 4.76 mmol) in water (5 ml) was added. The mixture was stirred overnight and then acidified with 1M hydrochloric acid, pH ~3–4. Dioxane was removed by evaporation in vacuum. The residue was diluted with water and then extracted with dichloromethane. The organic phase was washed with brine and dried with sodium sulfate. The solvent was then evaporated. 0.48 g desired product was obtained, yield 100%.

$^1$H-NMR (400 MHz, CDCl$_3$): 1.17 (3H, t), 1.23 (3H, t), 2.63 (2H, q), 2.93 (1H, dd), 3.06 (3H, m), 3.45 (1H, m), 3.58 (1H, m), 3.71 (3H, s), 4.04 (2H, dd), 4.14 (2H, t), 6.83 (2H, d), 7.15 (4H, 2d), 7.20 (2H,d)

Example 22

2-(Phenylthio-3-(4-{2-[4-(phenylthio)phenyl]ethoxy}phenyl)propan-1-ol

Ethyl 2-(phenylthio)-3-(4-{2-[4-(phenylthio)phenyl]ethoxy} phenyl)propanoate (0.65 g, 1.26 mmole) was dissolved in dry dichloromethane (15 ml) under argon. The solution was cooled to −78° C. and then DIBAL-H (1 M hexan solution, 2.6 ml, 2.90 mmole) was added. The cooling agent was removed after 0.5 h and after 3 h NH$_4$Cl (2M, 30 ml) and dichloromethane (30 ml) were added. The resulting mixture was filtered with suction. The filtercake was washed with dichloromethane and ethyl acetate. The phases of the filtrate was separated and the organic phase washed with water and then dried.

The desired product was obtained in 62% yield (0.373 g) after flash chromatography with heptane: dietyl ether (3:1)

$^1$H (300 MHz, CDCl$_3$): 2.12 (1H, t), 2.88 (2H, m), 3.07 (2H, t), 3.40 (1H, m), 3.47–3.65 (2H, m), 4.15 (2H, t), 6.85 (2-H, d), 7.15 (2H, d), 7.20–7.40 (14H, m)

$^{13}$C (75 MHz, CDCl$_3$): 12.7, 35.4, 36.8, 53.9, 62.5, 68.4, 114.6, 126.8, 128.9, 129.1, 129.2, 129.9, 130.2, 130.6, 130.8, 131.6, 132.7, 133.3, 133.4, 137.6, 157.5

The starting material is described in the priority application of WO9962871.

Example 23

4-[2-(4-{3-[Benzyl(ethyl)amino]-2-ethoxypropyl}phenoxy)ethyl]-N-methylaniline tert-Butyl 4-[2-(4-{3-[benzyl(ethyl)amino]-2-ethoxy-3-oxopropyl}phenoxy)ethyl]phenylcarbamate (5.2 g, 9.5 mmole) was dissolved in dry THF and cooled to 0° C. Borane methylsulfide (2 M, 11.9 ml, 23.8 mmole) was added dropwise. The reaction mixture was stirred at 0° C. for 0.5 hours after which it was allowed to reach room temperature and then refluxed for 5 hours. The reaction was quenched with water, extracted three times with ethyl acetate dried with magnesium sulfate and evaporated. The residue was redissolved in ethylacetate and chromatography on silica using a gradient system of ethylacetate:heptane (0–100%) gave 2.55 g (49% yield) of the desired product.

$^1$H-NMR (500 MHz; CDCl$_3$): δ 1.04 (t, 3H), 1.14 (t, 3H), 2.50–2.77 (m, 4H), 2.78–2.95 (m, 2H), 2.90 (s, 3H), 3.05 (t, 2H), 3.38–3.80 (m, 5H), 4.18 (t, 2H), 6.68 (d, 2H), 6.87 (d, 2H), 7.10–7.20 (m, 4H), 7.25–7.40 (m, 5H)

Starting Material (a) 3-(4-Benzyloxyphenyl)-2-ethoxyacrylic acid ethyl ester

Tetramethylguanidine (42.3 g; 0.37 mole) was slowly added to a solution of 4-benzyloxybenzaldehyde (75.6 g; 0.36 mole) and (1,2-diethoxy-2-oxoethyl) (triphenyl) phosphonium chloride (130.7 g; 0.304 mole) dissolved in chloroform (800 ml) at 0° C. After stirring at room temperature over night, the solvent was evaporated in vacuo. The residue was dissolved in diethyl ether, insoluble material was filtered off and the filtrate was washed with sodium bicarbonate and dried (magnesium sulfate). The procedure was repeated once and thereafter the crude product was stirred overnight with a sodium bisulfite saturated water solution. The solid material was filtered off, the product was extracted with diethyl ether, dried (magnesium sulfate) and the solvent was evaporated in vacuo to give 85 g (yield 73%) of the desired product.

(b) Ethyl 2-ethoxy-3-(4-hydroxyphenyl)propanoate

Compound (a) (62 g; 0.19 mole) was hydrogenated in ethyl acetate (400 ml) at atmospheric pressure using Pd/C (10%) as catalyst. The mixture was filtered through celite and evaporated in vacuo to give 45.6 g (yield 100%) of the desired product $^1$H-NMR (600 MHz; CDCl$_3$): 1.17 (t, 3H, J=7 Hz), 1.23 (t, 3H, J=7 Hz), 2.95 (d, 2H, J=6.6 Hz), 3.35–3.42 (m, 1H), 3.58–3.64 (m, 1H), 4.0 (t, 1H, J=6.6 Hz), 4.17 (q, 2H, J=7 Hz), 5.97 (s, 1 OH), 6.74 (dm, 2H, J=8.5 Hz, unresolved), 7.08 (dm, 2H, J=8.5 Hz, unresolved).

$^{13}$C-NMR (125 MHz; CDCl$_3$): 14.0, 14.8, 38.3, 61.0, 66.1, 80.3, 115.1, 128.2, 130.3, 154.8, 173.0.

(c) 4-(2-Hvdroxyethyl)phenylcarbamic acid tert-butyl ester

Di-tert-butyl dicarbonate (7.95 g; 36 mmole) was added to a mixture of p-aminophenethyl alcohol (5 g; 36 mmole) in THF at 0° C. After stirring at room temperature over night, the solvent was evaporated in vacuo to give 8 g (yield 94%) of the desired product.

$^1$H-NMR (400 MHz; DMSO-d$_6$): 1,5 (s, 9H), 2,65 (dd, 2H), 3,55 (dd, 2H), 4,6 (s, br, 1 OH), 7,1 (unresolved, 2H), 7,35 (unresolved, 2H), 9,1 (s, I NH).

$^{13}$C-NMR (100 MHz; DMSO-d$_6$): 28.3, 38.6, 62.5, 78.9, 118.3, 129.1, 133.2, 136.6, 153.0. 30

(d) Ethyl 3-{4-[2-(4-tert-butoxycarbonylaminophenyl)ethoxy]phenyl}-2-ethoxypropanoate Compound (c) (1.03 g; 4.34 mmole) and (b) (1.03 g; 4.34 mmole) were dissolved in dichloromethane under argon at room temperature. Azodicarbonyl dipiperidine (1.65 g; 6.5 mmole) and thereafter triphenylphosphine (1.37 g; 5.2 mmole) were added. After stirring at room temperature for 6 hours the solvent was evaporated in vacuo. Purification by chromatography on silica gel using heptane:ethyl acetate (2:1) as eluant gave 1.78 g (yield 89%) of the desired product $^1$H-NMR (400 MHz; CDCl$_3$): 1.17 (t, 3H, J=7 Hz), 1.23 (t, 3H, J=7 Hz), 1.53 (s, 9H),2.94–2.97 (m, 2H), 3.03 (t, 2H, J=7.1 Hz), 3.31–3.40 (m, 1H), 3.56–3.65 (m, 1H), 3.95–4.0 (m,1H), 4.11 (t, 2H, J=7.1 Hz), 4.17 (q, 2H, J=7 Hz), 6.60 (s, 1NH), 6.81 (dm, 2H, J=8.3 Hz, unresolved), 7.15 (dm, 2H, J=8.3 Hz, unresolved), 7.20 (dm, 2H, J=8.3 Hz, unresolved), 7.31 (dm, 2H, J=8.3 Hz, unresolved).

(e) 3-{4-[2-(4-tert-Butoxycarbonylaminophenyl)ethoxy]phenyl}-2-ethoxypropanoic acid Lithium hydroxide hydrate (77 mg; 1.85 mmole) in water (5.5 ml) was slowly added to a solution of ethyl 3-{4-[2-(4-tert-butoxycarbonylaminophenyl)ethoxy]phenyl}-2-ethoxypropanoate (0.77 g; 1.68 mmole) in THF (7.6 ml). After stirring at room temperature for 4 hours the reaction mixture was kept in a freezer for 4 days. THP was removed by evaporation in vacuo. More water was added and the mixture was acidified with hydrochloric acid to pH1. The product was extracted with ethyl acetate, washed twice with water, dried (sodium sulfate), filtered and the solvent was evaporated in vacuo to give 0.712 g (98.7% yield) of the desired product.

$^1$H-NMR (400 MHz; CDCl$_3$): 1.18 (t, 3H, J=7 Hz), 1.54 (s, 9H), 2.93–3.10 (m, 4H), 3.36–3.45 (m, 1H), 3.60–3.69 (m, 1H), 4.02–4.07 (m, 1H), 4.12 (t, 2H, J=7 Hz), 6.83 (dm, 2H, J=8.8 Hz, unresolved), 7.15–7.23 (m, 4H), 7.27–7.34 (m, 2H), 10.28 (bs, 1NH).

$^{13}$C-NMR (100 MHz; CDCl$_3$): 15.0, 28.3, 35.2, 38.0, 66.7, 68.8, 79.9, 80.7, 114.6, 119.1, 129.0, 129.4, 130.4, 133.1, 136.8, 153.2, 157.8, 175.3.

(f) tert-Butyl 4-[2-(4-{3-[benzyl(ethyl)amino]-2-ethoxy-3-oxopropyl}phenoxy)-ethyl]phenylcarbamate 3-{4-[2-(4-tert-Butoxycarbonylaminophenyl)ethoxy]phenyl}-2-ethoxypropanoic acid (6.09 g; 14.2 mmole) was dissolved in acetonitrile (150 ml) and the solution was cooled to 0° C. DCC (3.51 g; 17 mmole), HO—Su (1.96 g; 17 mmole) and DIPEA (2.2 g; 17 mmole) were added and stirred for 15 minutes before addition of N-ethylbenzylamine (2.72 g; 17 mmole). The reaction mixture was stirred overnight and then filtered and evaporated. Hydrochloric acid (2 M, 200 ml) was added to the residual oil and the obtained mixture was then extracted three times with ethyl acetate. The organic phase was washed with sodium hydrogencarbonate solution, dried with magnesium sulfate and evaporated. Chromatography of the residue on silica gel with heptane:ethylacetate (1.25–100%) using the gradient elution technique gave 5.32 g (68.5% yield) the desired product $^1$H-NMR (400 MHz; CDCl$_3$): 1.17 (t, 3H), 1.53 (s, 9H), 2.94–3.13 (m, 4H), 3.39–3.47 (m, 1H), 3.58–3.66 (m, 1H), 4.06–4.09 (m, 1H), 4.13 (t, 2H), 6.58 (b,1H), 6.77–6.85 (m, 3H), 7,17–7.23 (m, 3H), 7.26–7.32 (m, 2H11

$^{13}$C-NMR (100 MHz; CDCl$_3$): 15.0, 28.4, 35.2, 38.9, 66.9, 68.8, 79.7, 80.6, 113.2, 116.0, 119.1, 121.9, 129.2, 129.4, 133.2, 136.8, 138.3, 153.1, 158.9, 174.4

Example 24 tert-Butyl 4-[2-(4-{3-enzyl(ethyl)amino]-2-ethoxypropyl}phenoxy)ethyl]phenyl(methyl)carbamate Example 1 (2.55 g, 5.71 mmole) was dissolved in THF (50 ml) and sodium hydroxide (0.23 g, 5.7 mmole) dissolved in water (20 ml) and di-tert-butyldicarbonate (1.25 g, 5.7 mmole) were added. After stirring at room temperature for 48 hours it was checked using HPLC that all the starting material was consumed. Water was added, the TKF was evaporated and the residue extracted three times with ethyl acetate. The organic phase was dried with magnesium sulfate and evaporated. Purification of the crude product with preparative BPLC (Kromasil C8, 10 μm, 50×500 mm) using acetonitrile (60–80%) in ammonium acetate buffer (pH 7) as mobil phase gave 2.28 g (69% yield) of the desired product.

$^1$H-NMR (500 MHz; CDCl$_3$): 1.01 (t, 3H), 1.09 (t, 3H), 1.45 (s, 9H), 2.49–2.58 (m, 2H), 2.58–2.84 (m, 2H), 3.06 (t, 2H), 3.24 (s, 3H), 3.33–3.57 (m, 3H), 3.66 (q, 2H), 4.13 (t, 2H), 6.78 (d, 2H), 7.07 (d, 2H), 7.17 (d, 2H), 7.23 (d, 2H), 7.25–7.35 (m, 5H)

$^{13}$C-NMR (125 MHz; CDCl$_3$): 11.8, 15.8, 28.6, 35.6, 37.6, 38.9, 48.5, 57.1, 59.0, 65.5, 68.9, 79.8, 80.5, 114.5, 125.8, 127.2, 128.5, 129.3, 129.4, 130.7, 131.8, 135.7, 142.5, 155.2, 157.3

Example 25 tert-Butyl 4-[2-{4-[2-ethoxy-3-(ethylamino)propyl]phenoxy}ethyl]phenyl(methyl)carbamate Example 2 (1.0 g, 1.8 mmole) was dissolved in ethanol (100 ml). Acetic acid (0.12 g, 1.8 mmole) and palladium on activated carbon (5%, 0.5 g) was added. The mixture was stirred under hydrogen gas at room temperature. After 16 hours it was checked using HPLC that all the starting material was consumed.

The reaction mixture was filtered through celite, the solvent was evaporated and the residue extracted three times with ethyl acetate. The organic phase was dried with magnesium sulfate and evaporated giving 0.74 g (84% yield) of the desired product.

$^1$H-NMR (500 MHz; CDCl$_3$): 1.09 (t, 3H), 1.18 (t, 3H), 1.47 (s, 9H), 2.55–2.65 (m, 4H), 2.65–2.71 (m, 1H), 2.80–2.87 (m, 1H), 3.07 (t, 2H), 3.26 (s, 3H), 3.44–3.65 (m, 3H), 4.15 (t, 2H), 6.83 (d, 2H), 7.11 (d, 2H), 7.19 (d, 2H), 7.25 (d, 2H)

$^{13}$C-NMR (125 MHz; CDCl$_3$): 15.6, 15.9, 28.6, 35.5, 37.6, 38.5, 44.4, 53.3, 65.4, 68.8, 80.4, 80.6, 114.7, 125.7, 129.4, 130.6, 131.0, 135.7, 142.5, 155.1, 157.5

Example 26

4-[2-(4-{3-[Benzyl (ethyl)amino]-2-ethoxypropyl}phenoxy)ethyl]-N-methylaniline tert-Butyl 4-[2-(4-{3-[benzyl(ethyl)amino]-2-ethoxy-3-oxopropyl}phenoxy)ethyl]phenylcarbamate (5.2 g, 9.5 mmole) was dissolved in dry THF and cooled to 0° C. Borane methylsulfide (2 M, 11.9 ml, 23.8 mmole) was added dropwise. The reaction mixture was stirred at 0° C. for 0.5 hours after which it was allowed to reach room temperature and then refluxed for 5 hours. The reaction was quenched with water, extracted three times with ethyl acetate dried with magnesium sulfate and evaporated. The residue was redissolved in ethylacetate and chromatography on silica using a gradient system of ethylacetate:heptane (0–100%) gave 2.55 g (49% yield) of the desired product.

Starting Material (a) 3-(4-Benzyloxyphenyl)-2-ethoxyacrylic acid ethyl ester

Tetramethylguanidine (42.3 g; 0.37 mole) was slowly added to a solution of 4-benzyloxybenzaldehyde (75.6 g; 0.36 mole) and (1,2-diethoxy-2-oxoethyl) (triphenyl) phosphonium chloride (130.7 g; 0.304 mole) dissolved in chloroform (800 ml) at 0° C. After stirring at room temperature over night, the solvent was evaporated in vacuo. The residue was dissolved in diethyl ether, insoluble material was filtered off and the filtrate was washed with sodium bicarbonate and dried (magnesium sulfate). The procedure was repeated once and thereafter the crude product was stirred over night with a sodium bisulfite saturated water solution. The solid material was filtered off, the product was extracted with diethyl ether, dried (magnesium sulfate) and the solvent was evaporated in vacuo to give 85 g (yield 73%) of the desired product.

(b) Ethyl 2-ethoxy-,-(4-hydroxyphenyl)propanoate

Compound (a) (62 g; 0.19 mole) was hydrogenated in ethyl acetate (400 ml) at atmospheric pressure using Pd/C (10%) as catalyst. The mixture was filtered through celite and evaporated in vacuo to give 45.6 g (yield 100%) of the desired product $^1$H-NMR (600 MHz; CDCl$_3$): 1.17 (t, 3H, J=7 Hz), 1.23 (t, 3H, J=7 Hz), 2.95 (d, 2H, J=6.6 Hz), 3.35–3.42 (m, 1H), 3.58–3.64 (m, 1H), 4.0 (t, 1H, J=6.6 Hz), 4.17 (q, 2H, J=7 Hz), 5.97 (s, 1 OH), 6.74 (dm, 2H, J=8.5 Hz, unresolved), 7.08 (dm, 2H, J=8.5 Hz, unresolved)., $^{13}$C-NMR (125 MHz; CDCl$_3$): 14.0, 14.8, 38.3, 61.0, 66.1, 80.3, 115.1, 128.2, 130.3, 154.8, 173.0.

(c) 4-(2-Hydroxyethyl)phenylcarbamic acid tert-butyl ester

Di-tert-butyl dicarbonate (7.95 g; 36 mmole) was added to a mixture of p-aminophenethyl alcohol (5 g; 36 mmole) in THF at 0° C. After stirring at room temperature over night, the solvent was evaporated in vacuo to give 8 g (yield 94%) of the desired product.

$^1$H-NMR (400 MHz; DMSO-d$_6$): 1,5 (s, 9H), 2,65 (dd, 2H), 3,55 (dd, 2H), 4,6 (s, br, 1 OH), 7,1 (unresolved, 2H), 7,35 (unresolved, 2H), 9,1 (s, 1 NH).

$^{13}$C-NMR (100 MHz; DMSO-d$_6$): 28.3, 38.6, 62.5, 78.9, 118.3, 129.1, 133.2, 136.6, 153.0.

(d) Ethyl 3-{4-[2-(4-tert-butoxycarbonylaminopheny)ethoxy]phenyl}-2-ethoxypropanoate Compound (c) (1.03 g; 4.34 mmole) and (b) (1.03 g; 4.34 mmole) were dissolved in dichloromethane under argon at room temperature. Azodicarbonyl dipiperidine (1.65 g; 6.5 mmole) and thereafter triphenylphosphine (1.37 g; 5.2 mmole) were added. After stirring at room temperature for 6 hours the solvent was evaporated in vacuo. Purification by chromatography on silica gel using heptane:ethyl acetate (2:1) as eluant gave 1.78 g (yield 89%) of the desired product $^1$H-NMR (400 MHz; CDCl$_3$): 1.17 (t, 3H, J=7 Hz), 1.23 (t, 3H, J=7 Hz), 1.53 (s, 9H), 2.94–2.97 (m, 2H), 3.03 (t, 2H, J=7.1 Hz), 3.31–3.40 (m, 1H), 3.56–3.65 (m, 1H), 3.95–4.0 (m, 1H), 4.11 (t, 2H, J=7.1 Hz), 4.17 (q, 2H, J=7 Hz), 6.60 (s, 1NH), 6.81 (dm, 2H, J=8.3 Hz, unresolved), 7.15 (dm, 2H, J=8.3 Hz, unresolved), 7.20 (dm, 2H, J=8.3 Hz, unresolved), 7.31 (dm, 2H, J=8.3 Hz, unresolved).

(e) 3-{4-[2-(4-tert-Butoxycarbonylaminophenyl)ethoxy]phenyl}-2-ethoxypropanoic acid Lithium hydroxide hydrate (77 mg; 1.85 mmole) in water (5.5 ml) was slowly added to a solution of ethyl 3-(4-[2-(4-tert-butoxycarbonylaminophenyl)ethoxy]phenyl}-2-ethoxypropanoate (0.77 g; 1.68 mmole) in THF (7.6 ml). After stirring at room temperature for 4 hours the reaction mixture was kept in a freezer for 4 days. THF was removed by evaporation in vacuo. More water was added and the mixture was acidified with hydrochloric acid to pH 1. The product was extracted with ethyl acetate, washed twice with water, dried (sodium sulfate), filtered and the solvent was evaporated in vacuo to give 0.712 g (98.7% yield) of the desired product.

$^1$H-NMR (400 MHz; CDCl$_3$): 1.18 (t, 3H, J=7 Hz), 1.54 (s, 9H), 2.93–3.10 (m, 4H), 3.36–3.45 (m, 1H), 3.60–3.69 (m, 1H), 4.02–4.07 (m, 1H), 4.12 (t, 2H, J=7 Hz), 6.83 (dm, 2H, J=8.8 Hz, unresolved), 7.15–7.23 (m, 4H), 7.27–7.34 (m, 2H), 10.28 (bs, 1NH).

$^{13}$C-NMR (100 MHz; CDCl$_3$): 15.0, 28.3, 35.2,38.0, 66.7, 68.8, 79.9, 80.7, 114.6, 119.1, 129.0, 129.4, 130.4, 133.1, 136.8, 153.2, 157.8, 175.3.

(f) tert-Butyl 4-[2-(4-{3-[benzyl(ethyl)amino]-2-ethoxy-3-oxopropyl}phenoxy-ethyl]phenylcarbamate 3-{4-[2-(4-tert-Butoxycarbonylaminophenyl)ethoxy]phenyl}-2-ethoxypropanoic acid (6.09 g; 14.2 mmole) was dissolved in acetonitrile (150 ml) and the solution was cooled to 0° C. DCC (3.51 g; 17 mmole), HO—Su (1.96 g; 17 mmole) and DIPEA (2.2 g; 17 mmole) were added and stirred for 15 minutes before addition of N-ethylbenzylamine (2.72 g; 17 mmole). The reaction mixture was stirred over night and then filtered and evaporated. Hydrochloric acid (2 M, 200 ml) was added to the residual oil and the obtained mixture was then extracted three times with ethyl acetate. The organic phase was washed with sodium hydrogencarbonate solution, dried with magnesium sulfate and evaporated. Chromatography of the residue on silica gel with heptane:ethylacetate (1.25–100%) using the gradient elution technique gave 5.32 g (68.5% yield) the desired product $^1$H-NMR (400 MHz; CDCl$_3$): 1.17 (t, 3H), 1.53 (s, 9H), 2.94–3.13 (m, 4H), 3.39–3.47 (m, 1H), 3.58–3.66 (m, 1H), 4.06–4.09 (m, 1H), 4.13 (t, 2H), 6.58 (b,1H), 6.77–6.85 (m, 3H), 7.17–7.23 (m, 3H), 7.26–7.32 (m, 2H)

$^{13}$C-NMR (100 MHz; CDCl$_3$): 15.0, 28.4, 35.2, 38.9, 66.9, 68.8, 79.7, 80.6, 113.2, 116.0, 119.1, 121.9, 129.2, 129.4, 133.2, 136.8, 138.3, 153.1, 158.9, 174.4

Example 27 tert-Butyl 4-[2-(4-{3-[benzyl(ethyl)amino]-2-ethoxypropyl}phenoxy)ethyl]phenyl(methyl)carbamate Example 26 (2.55 g, 5.71 mmole) was dissolved in THF (50 ml) and sodium hydroxide (0.23 g, 5.7 mmole) dissolved in water (20 ml) and di-tert-butyldicarbonate (1.25 g, 5.7 mmole) were added. After stirring at room temperature 48 hours it was checked using HPLC that all the starting material was consumed. Water was added, the THF was evaporated and the residue extracted three times with ethyl acetate. The organic phase was dried with magnesium sulfate and evaporated. Purification of the crude product with preparative-HPLC (Kromasil C8, 10 µm, 50×500 mm) using acetonitrile (60–80%) in ammonium acetate buffer (pH 7) as mobil phase gave 2.28 g (69% yield) of the desired product.

$^1$H-NMR (500 MHz; CDCl$_3$): 1.01 (t, 3H), 1.09 (t, 3H), 1.45 (s, 9H), 2.49–2.58 (m, 2H), 2.58–2.84 (m, 2H), 3.06 (t, 2H), 3.24 (s, 3H), 3.33–3.57 (m, 3H), 3.66 (q, 2H), 4.13 (t, 2H), 6.78 (d, 2H), 7.07 (d, 2H), 7.17 (d, 2H), 7.23 (d, 2H), 7.25–7.35 (m, 5H)

$^{13}$C-NMR (125 MHz; CDCl$_3$): 11.8, 15.8, 28.6, 35.6, 37.6, 38.9, 48.5, 57.1, 59.0, 65.5, 68.9, 79.8, 80.5, 114.5, 125.8, 127.2, 128.5, 129.3, 129.4, 130.7, 131.8, 135.7, 142.5, 155.2, 157.3

Example 28 tert-Butyl 4-[2-{4-[2-ethoxy-3-(ethylamino)propyl]phenoxy}ethyl]phenyl(methyl)carbamate Example 27 (1.0 g, 1.8 mmole) was dissolved in ethanol (100 ml). Acetic acid (0.12 g, 1.8 mmole) and palladium on activated carbon (5%, 0.5 g) was added. The mixture was stirred under hydrogen gas at room temperature. After 16 hours it was checked using HPLC that all the starting material was consumed. The reaction mixture was filtered through celite, the solvent was evaporated and the residue extracted three times with ethyl acetate. The organic phase was dried with magnesium sulfate and evaporated giving 0.74 g (84% yield) of the desired product.

$^1$H-NMR (500 MHz; CDCl$_3$): 1.09 (t, 3H), 1.18 (t, 3H), 1.47 (s, 9H), 2.55–2.65 (m, 4H), 2.65–2.71 (m, 1H), 2.80–2.87 (m, 1H), 3.07 (t, 2H), 3.26 (s, 3H), 3.44–3.65 (m, 3H), 4.15 (t, 2H), 6.83 (d, 2H), 7.11 (d, 2H), 7.19 (d, 2H), 7.25 (d, 2H)

$^{13}$C-NMR (125 MHz; CDCl$_3$): 15.6, 15.9, 28.6, 35.5, 37.6, 38.5, 44.4, 53.3, 65.4, 68.8, 80.4, 80.6, 114.7, 125.7, 129.4, 130.6, 131.0, 135.7, 142.5, 155.1, 157.5

Example 29

1-Aminomethyl-2-[4-(2-{4-methylsulfonyloxyphenyl}ethoxy)phenyl-1-ethoxyethane hydrochloride 1-Carbamoyl-1-ethoxy-2-[4-(2-{4-methylsulfonyloxyphenyl}ethoxy)phenyl]ethane (0.8 g, 1.96 mmol) was dissolved in THF (10 ml, dry) and the solution was cooled in an ice-bath. Borane-methyl sulfide complex (2.0 M solution in diethyl ether, 2.5 ml, 5 mmol) was added. After a while, the cooling-bath was removed. The mixture was stirred for 0.5 hour and then heated to gently reflux for 6 hours. After cooling down to room temperature, hydrochloric acid (10%, 0.8 ml) was dropped in. The resulting mixture was stirred for 2 hours and then evaporated in vacuum until it was dry. The residue was treated with tetrahydrofuran/diethyl ether. White precipitates were formed and were filtered. 0.73 g of the desired product was obtained, yield 87%.

$^1$H NMR(300 MHz, CD$_3$OD): 1.19(t, J=7.5 Hz, 3H), 2.65–2.79(m, 2H), 2.88–2.98(m, 2H), 3.08(t, J=7 Hz, 2H), 3.19 (s, 3H), 3.44–3.54 (m, 1H), 3.60–3.74(m, 2H), 4.17 (t, J=7 Hz, 2H), 6.85 (d, J=9 Hz, 2H), 7.13 (d, J=9 Hz, 2H), 7.24 (d, J=9 Hz, 2H) and 7.39 (d, J=9 Hz, 2H).

$^{13}$C NMR(75 MHz, CD$_3$OD): 15.59, 36.07, 37.42, 37.88, 43.61, 66.23, 69.52, 78.0, 115.73 (2C), 123.16 (2C), 130.19, 131.56 (2C), 131.64 (2C), 139.64, 149.58 and 159.19.

Starting Material
(a) 2-Ethoxy-3-[4-(2-{4-methylsulfonyloxyphenl}ethoxy)phenyl]propanoic acid Lithium hydroxide hydrate (0.12 g; 2.82 mmole) dissolved in water (10 ml) was slowly added to a solution of ethyl 2-ethoxy-3-[4-(2-{4-methylsulfonyloxyphenyl}ethoxy)-phenyl]propanoate (described in Example 8) (1.12 g; 2.56 mmole) in TBF (30 ml). After stirring at room temperature for 3 hours, water (50 ml) was added and THF was removed by evaporation in vacuo. The residue was acidified with hydrochloric acid (2M), and extracted three times with ethyl acetate. The combined organic phases were dried with magnesiumsulfate. Evaporation of the solvent gave 1 g (yield 96%) of the desired product.

$^1$H-NMR (500 MHz; CDCl$_3$): 1.17 (t, 3H, J=7 Hz), 2.91–2.99 (m, 1H), 3.03–3.11 (m, 3H), 3.12 (s, 3H), 3.39–3.47 (m, 1H), 3.57–3.64 (m, 1H), 4.01–4.06 (m, 1H), 4.14 (t, 2H, J=6.7 Hz), 6.81 (dm, 2H, J=8.6 Hz, unresolved), 7.15 (dm, 2H, J=8.6 Hz, unresolved), 7.22 (dm, 2H, J=8.6 Hz, unresolved), 7.33 (dm, 2H, J=8.6 Hz, unresolved).

$^{13}$C-NMR (125 MHz; CDCl$_3$): 15.0, 35.1, 37.2, 37.8, 66.8, 68.1, 79.7, 114.4, 121.9, 128.8, 130.49, 130.52, 137.9, 147.8, 157.5, 169.1.

(b) 1-Carbamoyl 1-ethoxy-2-[4-(2-{4-methylsulfonyloxyphenyl}ethoxy)phenyl]ethane Ammonia was bubbled through a mixture of compound (a) (2.9 g; 7.1 mmole) and benzotriazol-1-yl-oxy-tris-pyrrolidino-phosphonium hexafluorophosphate (3.7 g; 7.1 n mmole) in DMF (30 ml) for 3 hours at room temperature. Water and ethyl acetate were added. The phases were separated, the organic phase was washed with water, dried with magnesium sulfate and the solvent was evaporated in vacuo. The crude product was crystallized in diethyl ether to give 2.5 g (yield 86%) of the desired product as a white powder.

$^1$H-NMR (300 MHz; CDCl$_3$): 1.13 (t, 3H, J=6.8 Hz), 2.80–2.90 (m, 1H), 3.05–3.14 (m, 6H), 3.36–3.56 (m, 2H), 3.84–3.91 (m, 1H), 4.14 (t, 2H, J=6.5 Hz), 5.38 (s br, I NH), 6.42 (s br, 1 NH), 6.80 (dm, 2H, J=8.8 Hz, unresolved), 7.15 (dm, 2H, J=8.8 Hz, unresolved), 7.19–7.27 (m, 2H), 7.34 (dm, 2H, J=8.1 Hz, unresolved). $^{13}$C-NMR (75 MHz; CDCl$_3$): 15.2, 35.2, 37.3, 38.0, 66.6, 68.1, 81.4, 114.2, 122.0, 129.7, 130.58, 130.64, 138.0, 147.8, 157.3, 175.2.

What is claimed is:
1. A compound of the general formula (I)

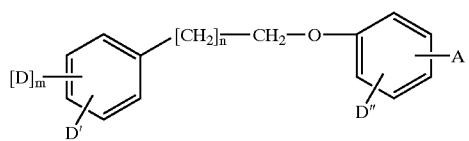

or a stereoisomer, optical isomer or racemate thereof or a pharmaceutically acceptable form of any of the above selected from the group consisting of a salt, a prodrug, a solvate, a crystalline form and any combination thereof, in which formula A is situated in the ortho, meta or para position and represents

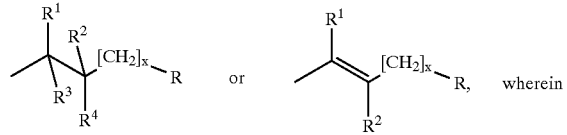

R is cyano, when X is 0, and when X is 1 then R is;
—BR$^a$ or SCOR$^a$, wherein B is O, S, SO or SO$_2$, wherein R$^a$ represents hydrogen, alkyl, aryl or alkylaryl and wherein the alkyl, aryl or alkylaryl group is optionally substituted one or more times by R$^b$, wherein R$^b$ represents alkyl, aryl, alkylaryl, cyano, —NR$^c$R$^c$, =O, halogen, —OH, —SH, -Oalkyl, -Oaryl, -Oalkylaryl, —COR$^c$, —SR$^d$, —SOR$^d$, or —SO$_2$R$^d$, wherein R$^c$ represents hydrogen, alkyl, aryl or alkylaryl and R$^d$ represents alkyl, aryl or alkylaryl;

—BB$^1$R$^a$, wherein B$^1$ is O when B is S, SO or SO$_2$ or B$^1$ is S, SO or SO$_2$ when B is O, and wherein B and R$^a$ are as defined above, or alternatively R is NR$^a$R$^a$, wherein each R$^a$ is the same or different and wherein R$^a$ is as defined above;

R$^2$ represents alkyl, halogen, aryl, alkylaryl, alkenyl, alkynyl, nitro or cyano and wherein the alkyl, aryl, alkenyl, alkylaryl or alkynyl group is optionally substituted by R$^b$, wherein R$^b$ is as defined above;

—BR$^a$ wherein B and R$^a$ are as defined above;
—SO$_2$NR$^a$R$^f$, wherein R$^f$ represents hydrogen, aryl or alkylaryl and R$^a$ is as defined above;
SO$_2$OR$^a$, wherein R$^a$ is as defined above;
—OCONR$^f$R$^a$, wherein R$^f$ and R$^a$ are as defined above;
—NR$^c$COOR$^d$, wherein R$^c$ and R$^d$ are as defined above;
—NR$^c$COR$^a$, wherein R$^c$ and R$^a$ are as defined above;

—CONR$^c$R$^a$, wherein R$^c$ and R$^a$ are as defined above;
—NR$^c$SO$_2$R$^d$, wherein R$^c$ and R$^d$ are as defined above; or
—NR$^c$CONR$^a$R$^k$, wherein R$^a$ and R$^c$ are as defined above and R$^k$ represents hydrogen, alkyl, aryl, or alkylaryl; or alternatively R$^2$ is —NR$^c$R$^a$, wherein R$^c$ and R$^a$ are as defined above;

R$^1$, R$^3$ and R$^4$ are the same or different and each represents hydrogen, alkyl, aryl, alkenyl, alkynyl, cyano, halogen or alkylaryl wherein the alkyl, aryl, alkenyl or alkynyl group is optionally substituted by R$^b$;

n is an integer from 1 to 6;

X is an integer 0 or 1;

m is an integer 0 or 1;

D is situated in the ortho, meta or para position and represents alkyl, acyl, aryl, alkylaryl, halogen, —CN or NO$_2$, wherein the alkyl, aryl, or alkylaryl group is optionally substituted by R$^b$;

—NR$^c$COOR$^a$, wherein R$^c$ and R$^a$ are as defined above;
NR$^c$COR$^a$, wherein R$^c$ and R$^a$ are as defined above;
—NR$^c$R$^a$, wherein R$^c$ and R$^a$ are as defined above;
NR$^c$SO$_2$R$^d$, wherein R$^c$ and R$^d$ are as defined above;
—NR$^c$CONR$^k$R$^c$, wherein R$^a$, R$^c$ and R$^k$ are as defined above
—NR$^c$CSNR$^a$R$^k$, wherein R$^a$, R$^c$ and R$^k$ are as defined above;
—OR$^a$, wherein R$^a$ is as defined above;
—OSO$_2$R$^d$, wherein R$^d$ is as defined above;
SO$_2$R$^d$, wherein R$^d$ is as defined above;
—SOR$^d$, wherein R$^d$ is as defined above;
—SR$^c$, wherein R$^c$ is as defined above;
—SO$_2$NR$^a$R$^f$, wherein R$^f$ and R$^a$ are as defined above;
—SO$_2$OR$^a$, wherein R$^a$ is as defined above;
—CONR$^c$R$^a$, wherein R$^c$ and R$^a$ are as defined above; or
—OCONR$^f$R$^a$, wherein R$^f$ and R$^a$ are as defined above;

D' is situated in the ortho, meta or para position and represents hydrogen, alkyl, acyl, aryl, alkylaryl, halogen, —CN, or —NO$_2$;
—NR$^f$R$^b$, wherein R$^f$ and R$^b$ are as defined above;
—OR$^f$, wherein R$^f$ is as defined above; or
—OSO$_2$R$^d$, wherein R$_d$ is as defined above; and D" is situated in the ortho, meta or para position and represents hydrogen, alkyl, acyl, aryl, alkylaryl, halogen, —CN, or —NO$_2$;
NR$^f$R$^b$ wherein R$^f$ and R$^b$ are as defined above;
—OR$^f$, wherein R$^f$ is as defined above; or
—OSO$_2$R$^d$, wherein R$^d$ is as defined above.

2. A compound of formula I as claimed in claim 1 wherein A is situated in the meta or para position and represents

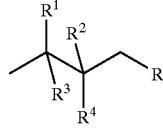

wherein R is
—BR$^a$;
—SCOR$^a$; or
—OSO$_2$R$^a$;
R$^1$, R$^3$ and R$^4$ are the same or different and each represents hydrogen, alkyl, aryl, alkenyl, alkynyl or cyano, wherein the alkyl, aryl, alkenyl or alkynyl group is optionally substituted by R$^b$;

R$^2$ represents alkyl, aryl, alkenyl, cyano or alkynyl and wherein the alkyl, aryl, alkenyl or alkynyl group is optionally substituted by R$^b$;
—BR$^a$;
—SO$_2$OR$^a$; —OCONR$^f$R$^a$;
NR$^c$COOR$^d$;
—NR$^c$COR$^a$; or
CONR$^c$R$^a$;

n is an integer from 1 to 2;

D is situated in the ortho, meta or para position and represents alkyl, acyl, aryl, alkylaryl, halogen, —CN, or NO$_2$, wherein the alkyl group is optionally substituted by R$^b$;
—OR$^a$;
—OSO$_2$R$^d$;
—OCONR$^a$R$^f$;
—NR$^c$COOR$^a$; or
—NR$^c$COR$^a$;
—SO$_2$R$^d$;
—SR$^c$;
CONR$^a$R$^c$; or
—NR$^c$R$^d$;

D' is situated in the ortho, meta or para position and represents hydrogen, alkyl, alkylaryl, halogen, —CN or —NO$_2$; or
—OR$^h$, wherein R$^h$ is hydrogen or alkyl; and D" is situated in the ortho, meta or para position and represent hydrogen, alkyl, alkylaryl, halogen, —CN or —NO$_2$; or
—OR$^f$.

3. A compound of formula I as claimed in claim 2 wherein
A is situated in the meta or para position,
R$^a$ is hydrogen, alkyl or alkylaryl;
R is —OR$^a$, —SR$^a$, —SCOR$^a$ or —OSO$_2$R$^a$;
R$^2$ is cyano;
—OR$^a$;
—NR$^c$COR$^a$; or
—CONR$^c$R$^a$;
—R$^1$, R$^3$ and R$^4$ are independently selected from hydrogen or alkyl;
D is situated in the ortho, meta or para position and represents alkyl optionally substituted by R$^b$; cyano;
—OR$^a$;
—NR$^c$COR$^a$;
—CONR$^c$R$^a$;
—NR$^c$COOR$^a$;
—OSO$_2$R$^d$;
—SO$_2$R$^d$; or
—OCONR$^c$R$^a$;

D' is hydrogen; and
D" is hydrogen.

4. A compound of formula I as claimed in claim 3 wherein
A is situated in the para position;
R is —OH, -Oalkyl or -Oalkylaryl;
—SCOR$^a$; or
—OSO$_2$R$^a$;
R$^1$ is hydrogen;
R$^2$ is -Oalkyl;
R$^3$ is hydrogen;

R⁴ is hydrogen;

n is the integer 1; and

D is situated in the para position, and represents
—NRʰCOORᵈ, wherein Rʰ represents hydrogen or alkyl;
—CONRᵃRᶜl
—SO₂Rᵈ;
—OSO₂Rᵈ;
—CN;
—ORᵃ; or
alkyl.

5. A compound of formula I as claimed in claim 4 wherein

R is
—ORᵃ;

R² is -Oalkyl; and

D is
—NRᶜCOORᵃ;
—CN; or
—OSO₂Rᵈ.

6. A compound of formula I as claimed in claim 3 wherein R¹, R³ and R⁴ are all hydrogen.

7. A compound of formula I as claimed in claim 3, wherein D is situated in the para position.

8. A compound of formula I as claimed in claim 7 wherein R¹, R² and R⁴ are all hydrogen.

9. A compound as claimed in claim 4 wherein R² is -Olower alkyl.

10. A compound selected from-one of the following:

3-[4-(2-{4-Cyanophenyl}ethoxy)phenyl]-2-ethoxypropanol;

2-Ethoxy-3-{3-[3-(4-methylsulfonyloxyphenyl)propoxy]phenyl}propanol;

3-{4-[2-(4-tert-Butoxycarbonylaminophenyl)ethoxy]phenyl}-2-ethoxypropanol;

3-{4-[2-(4-tert-Butoxycarbonylaminophenyl)ethoxy]phenyl}-(2R)-2-ethoxypropanol;

3-{4-[2-(4-tert-Butoxycarbonylaminophenyl)ethoxy]phenyl}-(2S)-2-ethoxypropanol;

3-[4-(2-{4-tert-Butoxycarbonylaminophenyl}ethoxy)phenyl]-2-ethoxypropyl methanesulfonate;

3-[4-(2-{4-tert-Butoxycarbonylaminophenyl}ethoxy)phenyl]-(2S)-ethoxypropyl methanesulfonate;

S-{3-[4-({4-tert-Butoxycarbonylaminophenyl}ethoxy)phenyl]-2-ethoxypropyl ethanethioate;

tert-Butyl N-(4–2-[4(2-ethoxy-3-mercaptopropyl)phenoxy]ethylphenyl)carbamate;

tert-Butyl N-[4-(2-(4-[{2S)-2-ethoxy-3-(ethylthio)propyl]phenoxy}ethyl)phenyl]carbamate;

2-Ethoxy-3-[4-(2-{4-methylsulfonyloxyphenyl}ethoxy)phenyl-1-hydroxypropane;

2-Ethoxy-3-[4-(2-{4-methylsulfonyloxyphenyl}ethoxy)phenyl-1-methoxypropane;

2-Cyano-3-{4-[2-(4-methylsulfonyloxyphenyl)ethoxy]phenyl}propanol;

2-Ethoxy-3-{4-[2-(4-ethyloxyphenyl)ethoxy]phenyl}propanol;

1-Cyano-2-[4-(2-{4-tert-butyloxycarbonylaminophenyl}ethoxy)phenyl]-1-ethoxyethane; or tert-Butyl 4-(2-{4-[(2S)-3-amino-2-ethoxypropyl]phenoxy}ethyl)phenylcarbamate.

11. A pharmaceutical formulation comprising a pcompound of formula I, as defined in any one of claims 1–10, and a pharmaceutically acceptable adjuvant, diluent or carrier.

12. A method for the treatment or prophylaxis of conditions associated with a patient having reduced sensitivity to insulin, which comprises administering to the patient an effective amount of a compound of formula I, as defined in any one of claims 1–5 and 6–10.

* * * * *

UNITED STATES PATENT AND TRADEMARK OFFICE
CERTIFICATE OF CORRECTION

PATENT NO. : 6,630,509 B2
DATED : October 7, 2003
INVENTOR(S) : Fägerhag et al.

It is certified that error appears in the above-identified patent and that said Letters Patent is hereby corrected as shown below:

<u>Column 40,</u>
Line 17, delete "the general".
Line 62, insert -- alkyl, acyl, -- after "hydrogen".
Line 64, "$SO_2OR^a$"" should read -- $–SO_2OR^a$ --.

<u>Column 41,</u>
Line 21, "$NR^cCOR^a$"" should read -- $–NR^cCOR^a$ --.
Line 23, "$NR^cSO_2R^d$"" should read -- $–NR^cSO_2R^d$ --.
Line 26, insert a semicolon after "above".
Line 31, "$SO_2R^d$"" should read -- $–SO_2R^d$ --.
Line 49, "$NR^fR^b$"" should read -- $–NR^fR^b$ --.

<u>Column 42,</u>
Line 9, "$NR^cCOOR^d$"" should read -- $–NR^cCOOR^d$ --.
Line 11, "$CONR^cR^a$"" should read -- $–CONR^cR^a$ --.
Line 26, "$CONR^aR^c$"" should read -- $–CONR^aR^c$ --.
Line 46, delete "$–R^1$" and substitute therefore -- $R^1$ --.

<u>Column 43,</u>
Line 7, delete "$–CONR^aR^c1$" and substitute therefor -- $–CONR^aR^c$; --.
Line 27, delete "$R^2$" and substitute therefor -- $R^3$ --.

<u>Column 44,</u>
Lines 12-13, "[{2S)" should read -- [(2S) -- and "phenoxy}ethyl" should read -- phenoxy)ethyl --.
Lines 28-29, delete "pcompound" and substitute therefor -- compound --.

Signed and Sealed this

Tenth Day of February, 2004

JON W. DUDAS
*Acting Director of the United States Patent and Trademark Office*